United States Patent
Doerr et al.

(10) Patent No.: US 12,087,403 B2
(45) Date of Patent: Sep. 10, 2024

(54) DNA ALIGNMENT USING A HIERARCHICAL INVERTED INDEX TABLE

(71) Applicant: COHERENT LOGIX, INCORPORATED, Austin, TX (US)

(72) Inventors: Michael B. Doerr, Hampton Falls, NH (US); Jan D. Garmany, Austin, TX (US); Stephen V. Wood, Hillsboro, OR (US); Daemon G. Anastas, Portland, OR (US); Martin A. Hunt, Austin, TX (US)

(73) Assignee: Coherent Logix, Incorporated, Austin, TX (US)

( * ) Notice: Subject to any disclaimer, the term of this patent is extended or adjusted under 35 U.S.C. 154(b) by 0 days.

(21) Appl. No.: 18/114,065

(22) Filed: Feb. 24, 2023

(65) Prior Publication Data
US 2024/0203527 A1 Jun. 20, 2024

Related U.S. Application Data

(63) Continuation of application No. 15/331,239, filed on Oct. 21, 2016, now Pat. No. 11,594,301.
(Continued)

(51) Int. Cl.
*G16B 30/10* (2019.01)
*G06F 16/22* (2019.01)
(Continued)

(52) U.S. Cl.
CPC ......... *G16B 30/10* (2019.02); *G06F 16/2228* (2019.01); *G06F 16/319* (2019.01);
(Continued)

(58) Field of Classification Search
CPC ..... A61K 38/00; C12N 15/11; G06F 16/2228; G06F 16/319; G06F 16/22
(Continued)

(56) References Cited

U.S. PATENT DOCUMENTS 7,702,640 B1   4/2010   Vermeulen et al.
11,842,796 B2 *  12/2023   Van Rooyen .......... G16B 50/00
(Continued)

FOREIGN PATENT DOCUMENTS

CN   101984445 A   3/2011
WO   2005096208 A1   10/2005
(Continued)

OTHER PUBLICATIONS

Office Action in Chinese Application No. 201680061446.2, dated Mar. 26, 2021, 10 pgs.
(Continued)

*Primary Examiner* — Hung T Vy
(74) *Attorney, Agent, or Firm* — Kowert, Hood, Munyon, Rankin & Goetzel, P.C.; Jeffrey C. Hood

(57) ABSTRACT

System and method for constructing a hierarchical index table usable for matching a search sequence to reference data. The index table may be constructed to contain entries associated with an exhaustive list of all subsequences of a given length, wherein each entry contains the number and locations of matches of each subsequence in the reference data. The hierarchical index table may be constructed in an iterative manner, wherein entries for each lengthened subsequence are selectively and iteratively constructed based on the number of matches being greater than each of a set of respective thresholds. The hierarchical index table may be used to search for matches between a search sequence and reference data, and to perform misfit identification and characterization upon each respective candidate match.

20 Claims, 9 Drawing Sheets
Specification includes a Sequence Listing.

Related U.S. Application Data

(60) Provisional application No. 62/244,541, filed on Oct. 21, 2015.

(51) Int. Cl.
  *G06F 16/31* (2019.01)
  *G16B 30/00* (2019.01)
  *G16B 50/00* (2019.01)
  *G16B 50/30* (2019.01)

(52) U.S. Cl.
  CPC ............ *G16B 30/00* (2019.02); *G16B 50/00* (2019.02); *G16B 50/30* (2019.02)

(58) Field of Classification Search
  USPC .......................................... 702/20; 707/741
  See application file for complete search history.

(56) References Cited

U.S. PATENT DOCUMENTS

| | | |
|---|---|---|
| 2004/0153255 A1 | 8/2004 | Ahn |
| 2009/0270277 A1 | 10/2009 | Glick et al. |
| 2009/0318310 A1 | 12/2009 | Liu |
| 2012/0089338 A1 | 4/2012 | Roth |
| 2014/0163900 A1 | 6/2014 | Erlich et al. |
| 2014/0214334 A1 | 7/2014 | Plattner et al. |
| 2014/0371109 A1* | 12/2014 | McMillen ............ H01L 23/528 702/20 |
| 2015/0248430 A1 | 9/2015 | Hospodor et al. |
| 2016/0292198 A1 | 10/2016 | Karten |
| 2017/0270243 A1 | 9/2017 | Karten |

FOREIGN PATENT DOCUMENTS

| | | |
|---|---|---|
| WO | 2014145503 A3 | 9/2014 |
| WO | 2015076671 A3 | 5/2015 |

OTHER PUBLICATIONS

Communication pursuant to Rules 70(2) and 70a(2) EPC and Supplementary European Search Report dated Jun. 17, 2019.

Wang Liang et al., "A new DNA alignment method based on inverted index," Jun. 30, 2013, https://arxiv.org/ftp/arxiv/papers/1307/1307.0194.pdf.

Wang Liang et al., "How to build a DNA search engine like Google?" Jun. 21, 2010, https://arxiv.org/ftp/arxiv/papers/1006/1006.4114.pdf.

"How to Build a Better DNA Search Engine—MIT Technology Review", Jun. 30, 2010, MIT Technology Review, https://www.technologyreview.com/s/419624/how-to-build-a-better-dna-search-engine/.

Liang Wang et al, "Segmenting DNA sequence into words," Feb. 12, 2012, https://arxiv.org/ftp/arxiv/papers/1202/1202_2518.pdf.

Chen, Shijian; Anqi Wang; and Lei M. Li—"SEME: A Fast Mapper of Illumina Sequencing Reads with Statistical Evaluation" Journal of Computational Biology, vol. 20, No. 11, 2013, pp. 847-860; Beijing, China (14 pages).

International Search Report for Application No. PCT/US16/58183, mailed Oct. 21, 2016 (4 pages).

Kim et al. "HISAT: a fast spliced aligner with low memory requirement" Nature Methods, vol. 12, No. 4, Apr. 2015 (Year: 2015).

Tolhuis, Bas—"GENALICE MAP: An Introduction To A New High Performance Read Alignment Solution" Dec. 2013; pp. 1-20; GENALICE BV, The Netherlands (20 pages).

* cited by examiner

| T | G | C | A | T | C | A | G | T | T | G | T | C | A | A | T | C | A | G | A | C | G | T |
|---|---|---|---|---|---|---|---|---|---|---|---|---|---|---|---|---|---|---|---|---|---|---|
| A | C | G | T | C | T | G | A | T | T | G | A | C | A | A | C | T | G | A | T | G | C | A |
| 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | initial -----

1st ext -------

2nd ext -----------

*FIG. 2*

| T | G | C | A | T | C | A | G | T | T | T | G | T | C | A | A | T | C | A | G | A | C | G | T |
|---|---|---|---|---|---|---|---|---|---|---|---|---|---|---|---|---|---|---|---|---|---|---|---|
| A | C | G | T | C | T | G | A | T | T | G | A | C | A | A | A | C | T | G | A | T | G | C | A |
| 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |

_ _ _ _ _ _ _ _ initial _ _ _ _ _ _ _ _ .

_ _ _ _ _ _ _ _ _ _ 1ˢᵗ ext _ _ _ _ _ .

_ _ _ _ _ _ _ _ _ _ _ _ 2ⁿᵈ ext _ _ _ _ .

amt_loc tables:

table 0:

| f | Ext | Amount | Location |
|---|---|---|---|
| / | 3 | N | L |
| .. | ... | ... | ... |
| S | 0 | N | L |
| / | 2 | N | L |
| / | 1 | N | L |
| .. | ... | ... | ... |
| S | 0 | N | L |

ACGT,0 → table 1:

| f | Ext | Amount | Location |
|---|---|---|---|
| / | 4 | N | L |
| .. | ... | ... | ... |
| / | 2 | N | L |
| / | 3 | N | L |
| / | 1 | N | L |
| .. | ... | ... | ... |
| S | 0 | N | L |

CT,L → table 2:

| f | Ext | Amount | Location |
|---|---|---|---|
| / | 4 | N | L |
| .. | ... | ... | ... |
| / | 2 | N | L |
| S | 0 | N | L |
| S | 0 | N | L |
| .. | ... | ... | ... |
| S | 0 | N | L |

GAT,L →

N of these:

bas_loc table 2:

| Candidate Locations |
|---|
| ppp |
| ... |
| ppp |
| ppp |
| ppp |
| ... |
| ppp |
| ... |
| ppp |

FIG. 7

SEQUENCE LISTING

```
Sequence total quantity: 16
SEQ ID NO: 1            moltype =    length =
SEQUENCE: 1
000

SEQ ID NO: 2            moltype = RNA   length = 24
FEATURE                 Location/Qualifiers
modified_base           4
                        mod_base = OTHER
                        note = thymine
modified_base           6
                        mod_base = OTHER
                        note = thymine
modified_base           9..10
                        mod_base = OTHER
                        note = thymine
modified_base           18
                        mod_base = OTHER
                        note = thymine
modified_base           21
                        mod_base = OTHER
                        note = thymine
misc_feature            1..24
                        note = Typical short read sequence
source                  1..24
                        mol_type = other RNA
                        organism = synthetic construct
SEQUENCE: 2
acgtctgatt gacaaactga tgca                                                24

SEQ ID NO: 3            moltype = RNA   length = 24
FEATURE                 Location/Qualifiers
modified_base           1
                        mod_base = OTHER
                        note = thymine
modified_base           5
                        mod_base = OTHER
                        note = thymine
modified_base           9..11
                        mod_base = OTHER
                        note = thymine
```

```
modified_base        13
                     mod_base = OTHER
                     note = thymine
modified_base        17
                     mod_base = OTHER
                     note = thymine
modified_base        24
                     mod_base = OTHER
                     note = thymine
misc_feature         1..24
                     note = Reversed and complemented typical short read sequence
source               1..24
                     mol_type = other RNA
                     organism = synthetic construct
SEQUENCE: 3
tgcatcagtt tgtcaatcag acgt                                              24

SEQ ID NO: 4         moltype = RNA  length = 24
FEATURE              Location/Qualifiers
modified_base        4
                     mod_base = OTHER
                     note = thymine
modified_base        9..10
                     mod_base = OTHER
                     note = thymine
modified_base        18
                     mod_base = OTHER
                     note = thymine
modified_base        21
                     mod_base = OTHER
                     note = thymine
misc_feature         1..24
                     note = Reference sequence in para.130 with 2 mifits
                      compared to short read of para.109
source               1..24
                     mol_type = other RNA
                     organism = synthetic construct
SEQUENCE: 4
aggtcagatt gacaaactga tgca                                              24

SEQ ID NO: 5         moltype = RNA  length = 24
FEATURE              Location/Qualifiers
modified_base        4
                     mod_base = OTHER
                     note = thymine
modified_base        6
                     mod_base = OTHER
                     note = thymine
modified_base        9..10
                     mod_base = OTHER
                     note = thymine
modified_base        18
                     mod_base = OTHER
                     note = thymine
modified_base        21
                     mod_base = OTHER
                     note = thymine
misc_feature         1..24
                     note = Reference sequence in para.133 with 3 mifits
                      compared to short read para.109
source               1..24
                     mol_type = other RNA
                     organism = synthetic construct
SEQUENCE: 5
acgtctgatt gacaaactga tgca                                              24

SEQ ID NO: 6         moltype = RNA  length = 28
FEATURE              Location/Qualifiers
modified_base        4
                     mod_base = OTHER
                     note = thymine
modified_base        6
                     mod_base = OTHER
                     note = thymine
modified_base        9..11
                     mod_base = OTHER
                     note = thymine
modified_base        22
                     mod_base = OTHER
```

```
                           note = thymine
modified_base              25
                           mod_base = OTHER
                           note = thymine
misc_feature               1..28
                           note = Reference sequence in para.136 with 4 mifits
                            compared to short read para.109
source                     1..28
                           mol_type = other RNA
                           organism = synthetic construct
SEQUENCE: 6
acgtctgatt tacggacaaa ctgatgca                                               28

SEQ ID NO: 7               moltype = RNA   length = 28
FEATURE                    Location/Qualifiers
modified_base              4
                           mod_base = OTHER
                           note = thymine
modified_base              6
                           mod_base = OTHER
                           note = thymine
modified_base              9..11
                           mod_base = OTHER
                           note = thymine
modified_base              22
                           mod_base = OTHER
                           note = thymine
misc_feature               1..28
                           note = Reference sequence in para.140 with 6 mifits
                            compared to short read para.109
source                     1..28
                           mol_type = other RNA
                           organism = synthetic construct
SEQUENCE: 7
acgtatgatt tacggacaaa ctgcggca                                               28

SEQ ID NO: 8               moltype = RNA   length = 20
FEATURE                    Location/Qualifiers
modified_base              4
                           mod_base = OTHER
                           note = thymine
modified_base              6
                           mod_base = OTHER
                           note = thymine
modified_base              9..11
                           mod_base = OTHER
                           note = thymine
misc_feature               1..20
                           note = Reference sequence in para.177 is the first 20 bases
                            of Sequence 6 Displaced by -4 bases from the short read,
                            it has 4 misfits to the short read
source                     1..20
                           mol_type = other RNA
                           organism = synthetic construct
SEQUENCE: 8
acgtctgatt tacggacaaa                                                        20

SEQ ID NO: 9               moltype = RNA   length = 21
FEATURE                    Location/Qualifiers
modified_base              4
                           mod_base = OTHER
                           note = thymine
modified_base              6
                           mod_base = OTHER
                           note = thymine
modified_base              9..11
                           mod_base = OTHER
                           note = thymine
misc_feature               1..21
                           note = Reference sequence in para.180 is the first 21 bases
                            of Sequence 6 Displaced by -3 bases from the short read,
                            it has 8 misfits to the short read,
source                     1..21
                           mol_type = other RNA
                           organism = synthetic construct
SEQUENCE: 9
acgtctgatt tacggacaaa c                                                      21

SEQ ID NO: 10              moltype = RNA   length = 22
```

| | | |
|---|---|---|
| FEATURE | Location/Qualifiers | |
| modified_base | 4 | |
| | mod_base = OTHER | |
| | note = thymine | |
| modified_base | 6 | |
| | mod_base = OTHER | |
| | note = thymine | |
| modified_base | 9..11 | |
| | mod_base = OTHER | |
| | note = thymine | |
| modified_base | 22 | |
| | mod_base = OTHER | |
| | note = thymine | |
| misc_feature | 1..22 | |
| | note = Reference sequence in para.183 is the first 22 bases of Sequence 6 Displaced by -2 bases from the short read, it has 6 misfits to the short read, | |
| source | 1..22 | |
| | mol_type = other RNA | |
| | organism = synthetic construct | |
| SEQUENCE: 10 | | |
| acgtctgatt tacggacaaa ct | | 22 |

| | | |
|---|---|---|
| SEQ ID NO: 11 | moltype = RNA  length = 23 | |
| FEATURE | Location/Qualifiers | |
| modified_base | 4 | |
| | mod_base = OTHER | |
| | note = thymine | |
| modified_base | 6 | |
| | mod_base = OTHER | |
| | note = thymine | |
| modified_base | 9..11 | |
| | mod_base = OTHER | |
| | note = thymine | |
| modified_base | 22 | |
| | mod_base = OTHER | |
| | note = thymine | |
| misc_feature | 1..23 | |
| | note = Reference sequence in para.186 is the first 23 bases of Sequence 6 Displaced by -1 bases from the short read, it has 7 misfits to the short read, | |
| source | 1..23 | |
| | mol_type = other RNA | |
| | organism = synthetic construct | |
| SEQUENCE: 11 | | |
| acgtctgatt tacggacaaa ctg | | 23 |

| | | |
|---|---|---|
| SEQ ID NO: 12 | moltype = RNA  length = 24 | |
| FEATURE | Location/Qualifiers | |
| modified_base | 4 | |
| | mod_base = OTHER | |
| | note = thymine | |
| modified_base | 6 | |
| | mod_base = OTHER | |
| | note = thymine | |
| modified_base | 9..11 | |
| | mod_base = OTHER | |
| | note = thymine | |
| modified_base | 22 | |
| | mod_base = OTHER | |
| | note = thymine | |
| misc_feature | 1..24 | |
| | note = Reference sequence in para.189 is the first 24 bases of Sequence 6 Displaced by 0 bases from the short read, it has 5 misfits to the short read, | |
| source | 1..24 | |
| | mol_type = other RNA | |
| | organism = synthetic construct | |
| SEQUENCE: 12 | | |
| acgtctgatt tacggacaaa ctga | | 24 |

| | | |
|---|---|---|
| SEQ ID NO: 13 | moltype = RNA  length = 24 | |
| FEATURE | Location/Qualifiers | |
| modified_base | 3 | |
| | mod_base = OTHER | |
| | note = thymine | |
| modified_base | 5 | |
| | mod_base = OTHER | |
| | note = thymine | |

```
modified_base            8..10
                         mod_base = OTHER
                         note = thymine
modified_base            21
                         mod_base = OTHER
                         note = thymine
modified_base            24
                         mod_base = OTHER
                         note = thymine
misc_feature             1..24
                         note = Reference sequence in para.192 is bases 2-25 from
                          Sequence 6 Displaced by +1 bases from the short read, it
                          has 6 misfits to the short read,
source                   1..24
                         mol_type = other RNA
                         organism = synthetic construct
SEQUENCE: 13
cgtctgattt acggacaaac tgat                                              24

SEQ ID NO: 14            moltype = RNA   length = 24
FEATURE                  Location/Qualifiers
modified_base            2
                         mod_base = OTHER
                         note = thymine
modified_base            4
                         mod_base = OTHER
                         note = thymine
modified_base            7..9
                         mod_base = OTHER
                         note = thymine
modified_base            20
                         mod_base = OTHER
                         note = thymine
modified_base            23
                         mod_base = OTHER
                         note = thymine
misc_feature             1..24
                         note = Reference sequence in para.195 is bases 3-26 from
                          Sequence 6 Displaced by +2 bases from the short read, it
                          has 8 misfits to the short read,
source                   1..24
                         mol_type = other RNA
                         organism = synthetic construct
SEQUENCE: 14
gtctgattta cggacaaact gatg                                              24

SEQ ID NO: 15            moltype = RNA   length = 24
FEATURE                  Location/Qualifiers
modified_base            1
                         mod_base = OTHER
                         note = thymine
modified_base            3
                         mod_base = OTHER
                         note = thymine
modified_base            6..8
                         mod_base = OTHER
                         note = thymine
modified_base            19
                         mod_base = OTHER
                         note = thymine
modified_base            22
                         mod_base = OTHER
                         note = thymine
misc_feature             1..24
                         note = Reference sequence in para.18 is bases 4-27 from
                          Sequence 6 Displaced by +3 bases from the short read, it
                          has 8 misfits to the short read,
source                   1..24
                         mol_type = other RNA
                         organism = synthetic construct
SEQUENCE: 15
tctgatttac ggacaaactg atgc                                              24

SEQ ID NO: 16            moltype = RNA   length = 24
FEATURE                  Location/Qualifiers
misc_feature             1..24
                         note = Reference sequence in para.18 is bases 4-28 from
                          Sequence 6 Displaced by +4 bases from the short read,
                          has 0 misfits to the short read
```

```
source                  1..24
                        mol_type = other RNA
                        organism = synthetic construct
modified_base           2
                        mod_base = OTHER
                        note = thymine
modified_base           5..7
                        mod_base = OTHER
                        note = thymine
modified_base           18
                        mod_base = OTHER
                        note = thymine
modified_base           21
                        mod_base = OTHER
                        note = thymine
SEQUENCE: 16
ctgatttacg gacaaactga tgca                                          24
```

DNA ALIGNMENT USING A HIERARCHICAL INVERTED INDEX TABLE

PRIORITY CLAIM

This application is a continuation of U.S. patent application Ser. No. 15/331,239, titled "DNA Alignment using a Hierarchical Inverted Index Table", filed Oct. 21, 2016, which claims benefit of priority to U.S. Application No. 62/244,541 titled "DNA Alignment", filed on Oct. 21, 2015, which are hereby incorporated by reference in their entirety as though fully and completely set forth herein.

This application includes herewith a sequence listing titled "Sequence listing 5860-04513" created on Mar. 6, 2024, and is 57,344 bytes, all of which is hereby incorporated by reference in its entirety. No new matter has been added.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, any disclaimer made in the instant application should not be read into or against the parent application or other related applications.

FIELD OF THE INVENTION

The application generally relates to mapping data patterns onto a reference data set, and more particularly to performing such data alignment or pattern matching in DNA sequencing and DNA alignment applications.

DESCRIPTION OF THE RELATED ART

Modern technology involves the collection and processing of increasingly large amounts of data. Applications and use cases of so called "Big Data" range from data mining, advertising, machine learning, and DNA sequencing, among many others. In many cases it is necessary to search for matches between a small sample of data and a much larger reference data set. As the size of the reference data set increases, the alignment of sample data to this reference data set (pattern matching) becomes an exponentially more computationally intensive task.

An exemplary case of data alignment occurs in the field of DNA alignment. Living organisms are composed of cells and the operation and reproduction of cells is controlled by genetic information that is passed from one generation of cells to the next.

Detailed knowledge of the genetic information of species and individual organisms holds great promise for more accurate life sciences supporting improved health care, agriculture, environmental management, and crime solving.

One of the obstacles to realizing these benefits is the cost to sequence the genetic information of an organism. The technology to do this has improved dramatically over the last couple of decades so that the goal of reducing the cost to less than US $1000 per individual human appears to be achievable. However, there remain problems of completeness, accuracy, interpretation of the data, and reliable diagnosis of disease. The number of days to acquire genetic information from a bio-sample is also an obstacle to uses that require fast response, such as the suitability of a pharmaceutical that is known to have severe side effects for susceptible individuals for use by an emergency room patient.

Accordingly, improved techniques and tools for data alignment, and DNA sequencing in particular, are desired.

SUMMARY OF THE INVENTION

Various embodiments are disclosed of a system and method for mapping a data pattern onto a significantly larger data set. In some embodiments, the larger data set may be a reference data set. In some embodiments, the larger data set may be the result of de novo sequencing, wherein a plurality of data patterns are used to construct a large data set that is self-consistent with the plurality of data patterns. Many of the embodiments presented herein relate to the specific use case of DNA alignment wherein the reference data set is a reference genome and the data pattern is a string of DNA bases derived from a short read (SR) of a DNA strand. However, the methods detailed herein are generally applicable to the problem of mapping any data pattern onto a larger data set. The description of the methods described herein in reference to DNA alignment is intended to facilitate exposition, and is not meant to be limiting in any way to the scope of the invention. Someone of skill in the art would easily see how the methods described herein may be applied to data alignment or pattern matching processes other than DNA alignment.

In one embodiment, a hierarchical index table based on reference data may be generated. The hierarchical index table may comprise the locations in the reference data where each of a plurality of data segments are located. In computer science, an index table of this form may be called an inverted index table. The hierarchical index table may be used to match a search sequence to the reference data. The index table may be constructed to contain entries associated with an exhaustive list of all subsequences of a given length, wherein each entry contains the number and locations of matches of each subsequence in the reference data. The hierarchical index table may be constructed in an iterative manner, wherein entries for each lengthened subsequence (deeper level of the hierarchy) are selectively and iteratively constructed based on the number of matches being greater than each of a set of respective thresholds. For some subsequences, the number of matches will be equal or less than the current threshold, for which the method makes a terminal entry in the table. The finite length of the reference data means that a sufficiently long subsequence can be found that will have a number of matches below a given positive number threshold. However, there are known to be subsequences of genomes that are more than 1000 bp long and occur thousands of times. These might be of interest to fully index or they might not; and in the latter case certain sequences might be filtered off instead of being included in the hierarchical index table.

A method for performing candidate location selection (identifying matching patterns) for a SR in a reference genome may include a search of a corresponding hierarchical index table, by performing the following in an iterative manner. A 'footprint' (comprised of a string of DNA bases) may be generated based on a segment of the SR, and used to select at least one candidate location of the SR from the index table associated with the reference genome. The length of the footprint may be extended in order to move to a deeper level of the hierarchical index table. Once a terminal entry of the hierarchical index table is reached, the iterations may cease, and the candidate locations may be output. The use of the hierarchical index table may operate to greatly increase the speed by which candidate selection may occur.

In some embodiments, the method may further include evaluating each candidate location in the SR. For example, in some embodiments, for each candidate location, matches between the SR and the reference genome may be determined based on a number of base errors between the SR and the reference genome. In some embodiments, the evaluating may further include determining at least one insertion or deletion (collectively referred to as indels) in the SR. For example, an anchor position in the SR may be determined based on number of lo-end and hi-end misfits of the SR. Length and type of the at least one indel may be determined using the anchor position. A starting position of the at least one indel may be determined. In one embodiment, determining the starting position may include computing a first running error sum between the SR and the reference genome at the candidate location, and computing a second running error sum between the SR and the reference genome at an offset from the candidate location, where the offset is based on the type and length of the at least one indel. The starting location of the at least one indel may then be determined based on a minimum of the first and second running error sums.

BRIEF DESCRIPTION OF THE DRAWINGS

A better understanding of the present invention can be obtained when the following detailed description of the preferred embodiment is considered in conjunction with the following drawings, in which:

FIG. 2 illustrates a short read (SR) with exemplary bases ACGTCTGATTGACAAACTGATGCA, according to one embodiment;

FIG. 7 illustrates the present alignment technique applied to the sequence of FIG. 2, according to one embodiment;

Figure 1:
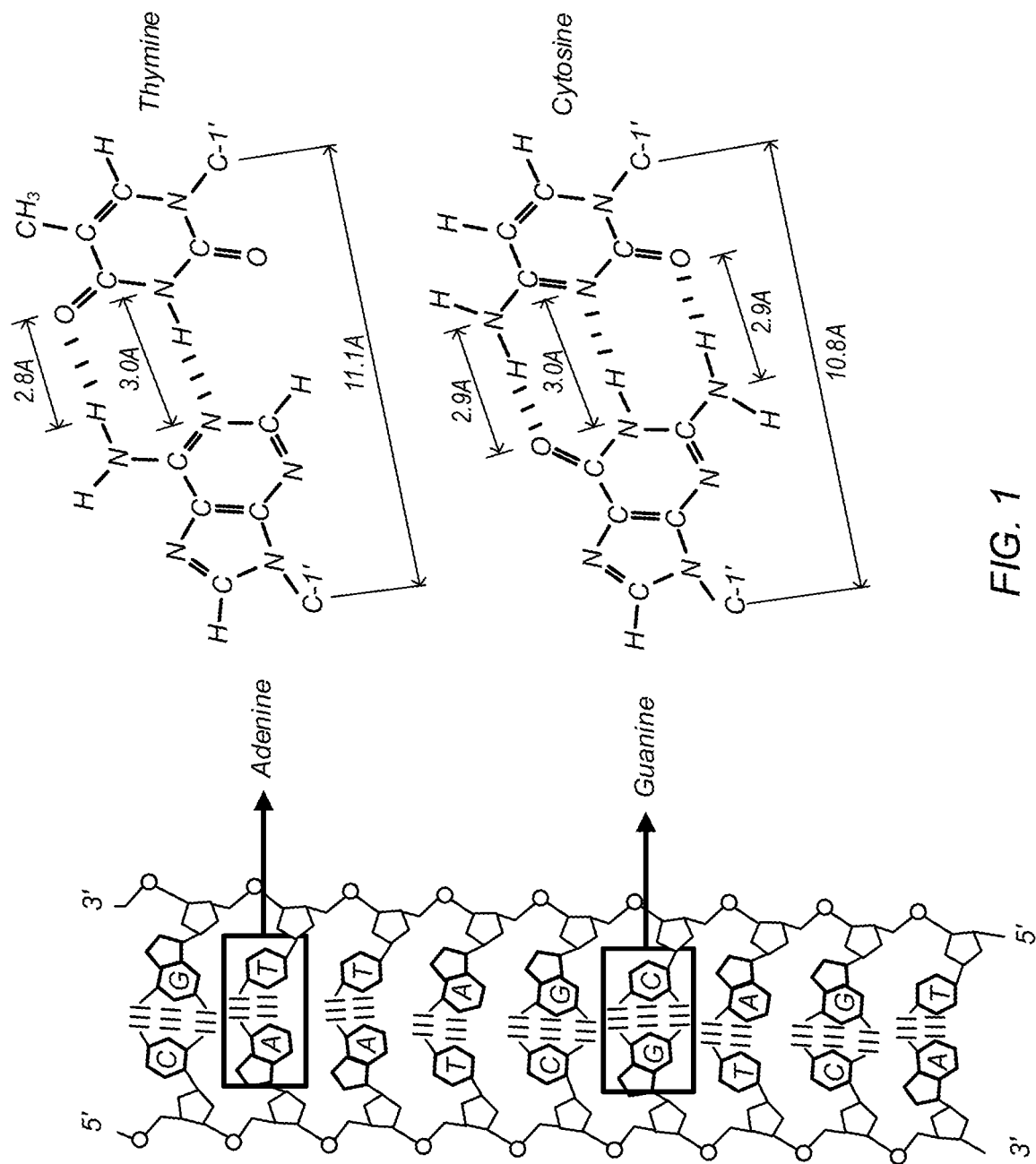
FIG. 1 illustrates two exemplary DNA sequences, specifically showing complemented and reversed order of bases in the two strands, according to one embodiment.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF EMBODIMENTS OF THE INVENTION

Incorporation by Reference

The following patents/applications are hereby incorporated by reference in their entirety as though fully and completely set forth herein:

U.S. Pat. No. 7,415,594 titled "Processing System with Interspersed Stall Propagating Processors and Communication Elements filed on Jun. 24, 2003, whose inventors are Michael B. Doerr, William H. Hallidy, David A. Gibson, and Craig M. Chase.

U.S. patent application Ser. No. 13/274,138, titled "Disabling Communication in a Multiprocessor System", filed Oct. 14, 2011, whose inventors are Michael B. Doerr, Carl S. Dobbs, Michael B. Solka, Michael R Trocino, and David A. Gibson.

Terms

The following is a glossary of terms used in the present application:

Memory Medium—Any of various types of memory devices or storage devices.

The term "memory medium" is intended to include an installation medium, e.g., a CD-ROM, floppy disks 104, or tape device; a computer system memory or random access memory such as DRAM, DDR RAM, SRAM, EDO RAM, Rambus RAM, etc.; or a non-volatile memory such as a magnetic media, e.g., a hard drive, optical storage, or ROM, EPROM, FLASH, etc. The memory medium may comprise other types of memory as well, or combinations thereof. In addition, the memory medium may be located in a first computer in which the programs are executed, and/or may be located in a second different computer which connects to the first computer over a network, such as the Internet. In the latter instance, the second computer may provide program instructions to the first computer for execution. The term "memory medium" may include two or more memory mediums which may reside in different locations, e.g., in different computers that are connected over a network.

Carrier Medium—a memory medium as described above, as well as a physical transmission medium, such as a bus, network, and/or other physical transmission medium that conveys signals such as electrical or optical signals.

Programmable Hardware Element—includes various hardware devices comprising multiple programmable function blocks connected via a programmable or hardwired interconnect. Examples include FPGAs (Field Programmable Gate Arrays), PLDs (Programmable Logic Devices), FPOAs (Field Programmable Object Arrays), and CPLDs (Complex PLDs). The programmable function blocks may range from fine grained (combinatorial logic or look up tables) to coarse grained (arithmetic logic units or processor cores). A programmable hardware element may also be referred to as "reconfigurable logic".

Application Specific Integrated Circuit (ASIC)—this term is intended to have the full breadth of its ordinary meaning. The term ASIC is intended to include an integrated circuit customized for a particular application, rather than a general purpose programmable device, although ASIC may contain programmable processor cores as building blocks. Cell phone cell, MP3 player chip, and many other single-function ICs are examples of ASICs. An ASIC is usually described in a hardware description language such as Verilog or VHDL.

Program—the term "program" is intended to have the full breadth of its ordinary meaning. The term "program" includes 1) a software program which may be stored in a memory and is executable by a processor or 2) a hardware configuration program useable for configuring a programmable hardware element or ASIC.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, e.g., imperative or procedural languages, such as C, C++, PASCAL, FORTRAN, COBOL, JAVA, assembly language, etc.; graphical programs (programs written in graphical programming languages); assembly language programs; programs that have been compiled to machine language; scripts; and other types of executable software. A software program may comprise two or more software programs that interoperate in some manner.

Hardware Configuration Program—a program, e.g., a netlist or bit file, that can be used to program or configure a programmable hardware element or ASIC.

Computer System—any of various types of computing or processing systems, including a personal computer system (PC), mainframe computer system, workstation, network appliance, Internet appliance, personal digital assistant (PDA), grid computing system, or other device or combinations of devices. In general, the term "computer system" can be broadly defined to encompass any device (or combination of devices) having at least one processor that executes instructions from a memory medium.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Development Process—refers to the life-cycle for development based on a methodology. At a coarse level it describes how to drive user requirements and constraints through design, implementation, verification, deployment, and maintenance.

Overview: DNA Sequencing

For carbon-based life-forms, genetic information is encoded in long chain molecules of deoxyribonucleic acid (DNA), where two parallel spines of alternating sugar and phosphate groups are held together by a ladder of base pairs. The two spines protect the base pairs and gently twist about each other to form a double helix configuration. Longer chains of DNA form coils, and coils of coils. For larger organisms these coils are organized into chromosomes, which are visible with optical microscopes at very high magnification.

Each base is one of the set {Adenine, Thymine, Cytosine, Guanine}. Each Adenine base will pair only with a Thymine, and each Cytosine will pair only with a Guanine. These pairing rules support replication of DNA. When DNA is combined with a certain enzyme in solution, the double helix unzips into a pair of single strands each composed of a single spine and attached bases. Then, in a soup of bases, sugars, phosphates and enzyme, for each strand, a complementary strand may be assembled using the original strand as a template. The net result is the duplication of the original double helix into a pair of double helixes. Replication in vitro can be repeated to produce as much DNA as physically needed to supply a sequencing machine; however, for speed and cost reasons, sequencing machines have evolved to use smaller and smaller amounts of DNA.

FIG. 1 illustrates two exemplary DNA strands, specifically showing complemented and reversed order of bases in the two strands. As FIG. 1 shows, a chain of phosphate groups (small circles) and deoxyribose sugar (pentagons) serves as a spine for the single DNA strands, separating the nucleic bases for stable and predictable hydrogen-bond coupling between paired bases. The non-planar form of the sugar rings and the electronic configuration of the nitrogen atoms in the bases ensure predictable assembly of the DNA strand and the coupling of each base with its complementary base in the other strand.

Sequencing machines use many methods to determine the sequence of bases in a strand of DNA. Although each method is different, the industry has settled on a few defacto standard formats for reporting the raw sequence data. For single strand reads, these formats report the base sequence in the 5' to 3' direction. This notation refers to the carbon atoms in the deoxyribose moiety that couple to the adjacent phosphate groups. The 5' atom is not part of the 5-member ring in the sugar, but is instead the "elbow" that extends to the previous phosphate, where the sense of "previous" is defined in terms of the 5' to 3' convention. FIG. 1 illustrates this numbering convention, where the 1' site provides the bond to the available nitrogen orbital in the base. The 2' site is where an oxygen atom has been removed from the ribose to form deoxyribose.

As FIG. 1 indicates, the 5' to 3' sequence is CAATCGTCA on the left and TGACGATTG on the right, illustrating the complemented and reversed order of the bases in the other strand. Note that specific bonds for each nucleotide are shown on the right.

A fragment of DNA can be represented by a string of letters corresponding to the sequence of bases along one of the spines in the 5' to 3' direction, for example, ACGTCT-GATTGACAAACTGATGCA. From the chemistry, it is known that the sequence of bases on the complementary spine in the original direction is the complemented string, TGCAGACTAACTGTTTGACTACGT. However, a sequencer machine will not be reading a double helix but only single strands, and it will report the complementary strand, in the 5' to 3' direction for that strand as TGCATCAGTTTGTCAATCAGACGT, which is the reverse-complement of the original. FIG. 2 shows an example strand of DNA with its complement strand. When processing the raw data it is important to know that the same genetic information is encoded in both strands. When aligning a short read to a reference genome, it is necessary to attempt alignment for both the original short read and the reverse complement of the short read.

In the prior art, no reliable machine method has been developed to sequence DNA strands beyond about 2000 base pairs (bp) in a single shot [the Sanger method routinely does ~800 bp]. However, longer strands can be attached to a substrate and sequenced from both ends, resulting in a pair of reads that are related by a target separation measurable in number of base pairs. In all cases the read sequences are very much shorter than the number of base pairs in a single human chromosome which may contain a DNA sequence with up to about 249 million base pairs (Chromosome 1). For all 23 chromosomes in the human genome there are about 3.2 billion base pairs.

Automated high speed sequencer machines are used to analyze a biological sample from a single individual to produce billions of relatively short reads (SR), on the order of 100 bp (base pairs) per SR. Then high speed computers are used to compare billions of short reads with each other and to search for overlaps where the sequences match.

De Novo Sequencing

With enough overlaps, a picture of a very long sequence can be built up. This is referred to as de novo sequencing. If a full sequence for an individual is built up (23 chromosomes in the case of a human), then we have the genetic information for that individual. The combination of genes from many individuals, enough to cover the variations of the species, is called the genome for that species. For many species, the mitochondria in the cells also contain DNA with additional genetic information for the genome.

Resequencing

Once a reference genome is established, the process of obtaining the gene information of an individual and matching the raw reads to the reference genome is called resequencing. The search for locations in the reference genome where a read sequence has a full or near match is called alignment or mapping. Thus a full resequencing may require many billions of alignments.

Resequencing may be used to identify susceptibilities to diseases with a genetic basis, and identify susceptibilities to side effects of pharmaceuticals, etc. Comparison of genes between individuals may be used to show family relationships. For resequencing, a reference genome database already exists and it may be indexed to speed up each alignment process. Embodiments detailed below present a novel and advantageous method for constructing a hierarchical index table based on a reference genome database.

Once the index table is constructed, it may be searched a huge number of times at high speed to align a large set of raw-data reads. Each alignment may be processed independently of the others, which lends it to processing on massively parallel computers. However, there may be advantages to sharing some information between alignments. For example, if a read is found to not match anything in the target genome it may be put in a list of reads to be pre-rejected without searching again. Such un-matchable reads may come from bacterial DNA that was part of the original sample.

A trend in DNA sequencer machine design is to produce shorter reads more prolifically and more rapidly. A typical set of raw data from an individual human might be many billion short reads (SR), each one averaging about 100 bp in length. These may be single-strand reads or paired-reads. Paired-reads may have target separations from a few bp to hundreds, perhaps thousands of bp. Each SR is made with a certain amount of noise and the machines that do the SR produce a quality metric for each base in the read. This per-base quality information can be used to improve alignment of each SR to the genome. Raw data sets may contain additional DNA from bacteria that will not match the human genome, and these reads should be filtered off either before or during alignment processing.

Figure 3:
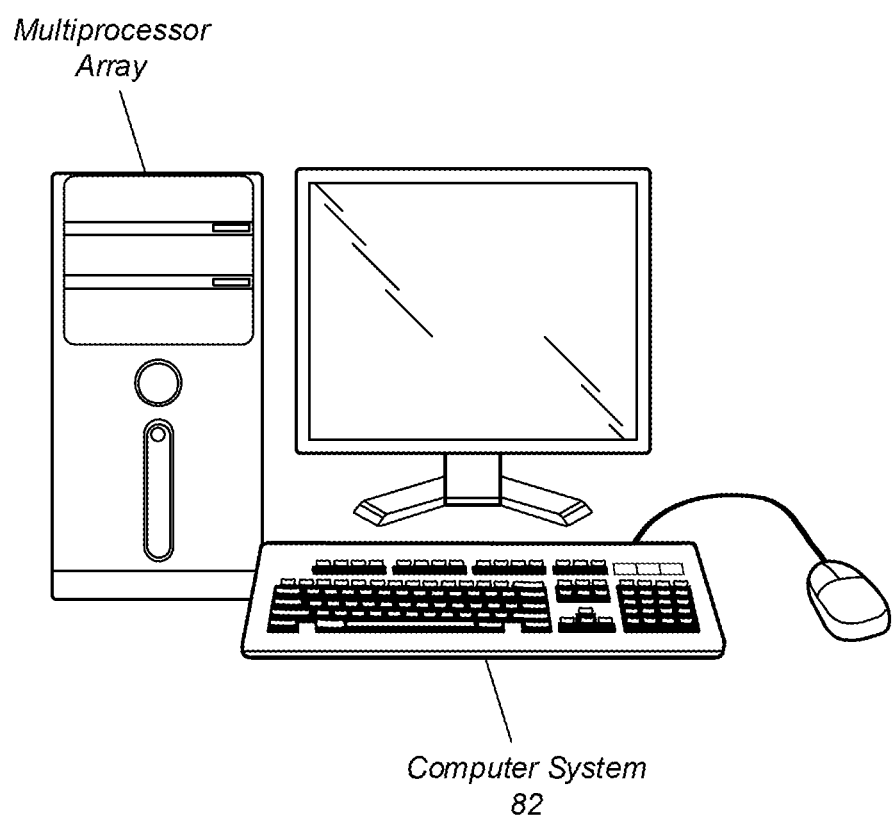
FIG. 3 illustrates an exemplary system configured to implement embodiments of the present techniques.

FIG. 3: Exemplary System

FIG. 3 illustrates an exemplary system configured to implement embodiments of the present techniques. As shown, in some embodiments, the system may be the computing system 82, such as a workstation, and may include one or more processors and at least one memory medium on which one or more computer programs or software components according to embodiments of the present techniques may be stored. For example, the memory medium may store one or more programs which are executable by the one or more processors to perform the methods described herein. The memory medium may also store operating system software, as well as other software for operation of the computer system.

In some embodiments, the system may include a multi-processor array (MPA) configured to implement the techniques disclosed herein. For example, the MPA may implement a processing system with interspersed processors and communication elements and/or may have a HyperX architecture, as described in U.S. Pat. No. 7,415,594, which was incorporated by reference above.

Embodiments of the invention may also be implemented by at least one programmable hardware element, such as a Field Programmable Gate Array (FPGA), or by a combination of a programmable hardware element and one or more software programmable processors.

It should be noted, however, that the computing system 82 shown in FIG. 3 is meant to be exemplary only, and that any other computing system may be used as desired.

System Aspects

The present technique may include a data flow system that overlaps data input and output and pre- and post-processing with the core alignment functions. One embodiment uses communication sockets and double buffering techniques to accomplish this.

Processing of pairs of SR may be performed during the core alignment phase. This may be accomplished by considering potential mate pairs during the alignment of individual SR and the hierarchy of possible alignment types.

In order to speed up the core alignment tasks, ancillary information not needed for alignment may be passed to the post alignment stages, which may reduce bandwidth and memory requirements in the core aligner. One embodiment uses a separate set of communication sockets to accomplish this.

Exemplary Embodiments and Implementations

The following describes various exemplary embodiments and implementations of the techniques disclosed herein. However, it should be noted that the particular embodiments and techniques described do not limit the invention to any particular form, function, or appearance.

DNA alignment may refer to the process of finding the location(s) at which a given DNA fragment (i.e., a short read, or SR) occurs within a reference genome.

A SR may comprise many DNA bases, wherein each base is one of the four found in DNA, (adenine, cytosine, guanine, and thymine) which are abbreviated as A, C, G or T. The length of each SR may typically be around 100 bases long depending on the sequencing method used. A trend for newer sequencing methods has been to produce shorter SRs but more of them per unit time. As noted each SR may have some base errors due to noise from the sequencing method. These errors may be mitigated by redundancy and by using the per-base quality information that comes with each SR. To characterize an individual human it is desirable to have about 50× redundant coverage of the entire genome by SRs. Given that a reference human genome contains over 3 billion bases, the ensemble of SR data from one individual may have 150-200 billion bases in it. Each SR may be compared to the genome to discover where it fits. Clearly it is desirable to use very efficient searching of the genome to process the large amount of SR data from an individual.

The time required for DNA alignment may be significantly reduced by encoding the reference genome into a hierarchical inverted index table. A novel form and method for such an inverted index table, and more specifically for a hierarchical inverted index table, is given below.

In one embodiment, a 2-phase approach for aligning a given SR to an index table may be used. The first phase may be referred to as candidate selection, followed by the second phase, which may be referred to as candidate evaluation.

Candidate selection may generate a list of potential locations which may be subsequently evaluated for accuracy. Because the candidate evaluation phase is potentially very time-consuming, it is important that the candidate selection phase reduce the number of candidate locations intelligently.

It should be noted that these (phase) names are meant to be illustrative and exemplary only, and that any other names may be used as desired. Additionally, in various embodiments, the functionality of these two phases may be organized or arranged in different ways, e.g., split into more than two phases, partitioned differently, etc., and still implement the novel techniques disclosed herein.

Figure 4:
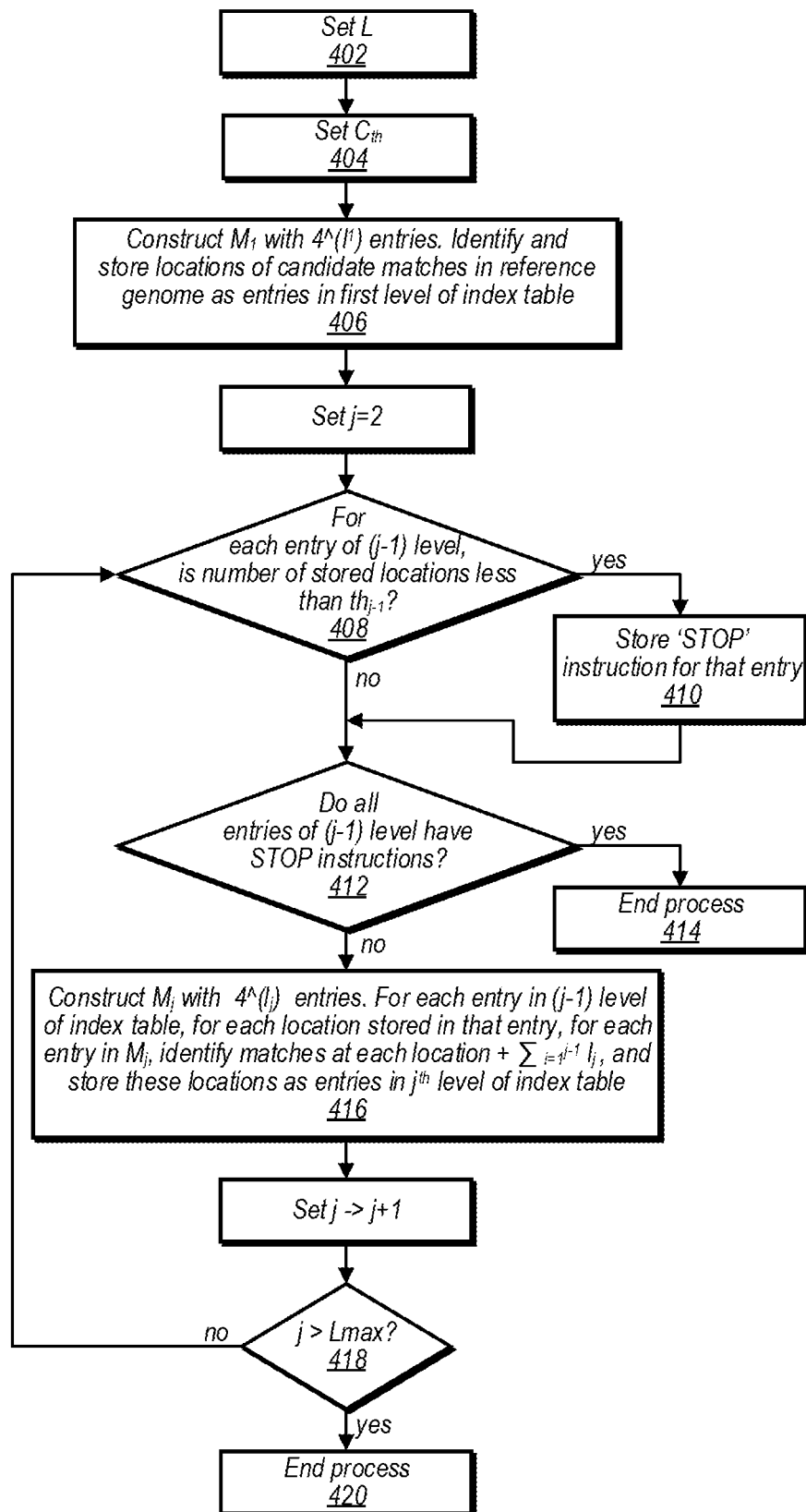
FIG. 4 is a flowchart diagram illustrating an algorithm for constructing a hierarchical index table, in some embodiments.

FIG. 4—Algorithm for Construction of a Hierarchical Index Table

FIG. 4 shows an exemplary algorithm for constructing a hierarchical inverted index table from a reference genome. The term "inverted index table" is a term of art in computer science and refers to an index data structure that stores entries that contain a mapping from content, such as data (e.g., numbers or words) to locations of this content in a data set. One everyday example of an "inverted index" is the index of a book, which contains a listing of words or phrases appearing in the book, each followed by locations in the book where this respective word or phrase can be found. For the sake of convenience, the term "index table" is used herein to refer to what is known in the computer literature as an "inverted index table." The term "hierarchical" used in the term "hierarchical inverted index table" refers to entries of the index table having various levels in a hierarchical manner, as explained further below.

In some embodiments of the present technique, a hierarchical index table may be constructed using a set of k-mers (a string of k bases) to efficiently determine a set of candidate locations. The index table is generated once for a reference genome, and then can be used by all sets of SRs to be aligned to that reference genome. It may be appreciated that the methods described herein may be more broadly performed on any reference data, and may be used by any set of subsequences to be aligned to that reference data.

In creating a hierarchical index table, a computing device may be configured to store reference data (the genome) into memory. The computing device may then create a hierarchical index table based on the reference data by creating a plurality of entries at a plurality of levels. As explained in much greater detail below, construction of the index table begins with creation of first level entries (level 1) which comprise information on a (preferably exhaustive) list or set of subsequences of a predetermined length (or portions of a data set of a predetermined size). The information may comprise location information of each respective subsequence in the reference genome.

For each entry at each respective level n, where n is a non-zero positive integer, the computing device may be configured to create additional n+1 level entries for respective level n entries in the hierarchical index table if matching criteria of the respective level n entry are greater than a threshold. Each n+1 level entry may add additional lengths to the subsequence in the previous level, thus creating a longer subsequence for potential matching. Similar to the first level entry, each n+1 level entry contains location information of each respective longer subsequence in the reference genome. This creation of additional levels of longer subsequences continues until the matching criteria is no longer satisfied—the number of matches at the terminal entry (the last entry in a hierarchical branch) is lower than a threshold. It is noted that use of a lower threshold may operate to reduce the number of matches at each terminal entry. In contrast, use of higher thresholds may help to reduce the overall number of entries in the index table. It is noted that different threshold values may be used at different levels of the hierarchy. Thus, in the resulting completed hierarchical index table, different respective level 1 entries may have differing numbers of subsequent levels of hierarchy that are derived from that respective level 1 entry, where the number of subsequent levels of hierarchy depend on the number of matches at each subsequent level.

Thus the index table may be characterized as hierarchical or multi-level. Upon completion of the construction of the hierarchical index table, the computing device may be configured to receive input specifying a search sequence, and may use the hierarchical index table to search for matches of a subsection of the search sequence in the reference data at a greatly expedited rate.

In some exemplary embodiments, an algorithm may be used to construct a hierarchical index table as follows. A coding scheme may be selected for encoding the four base pairs in a binary format. In some embodiments, a 2-bit coding scheme may be used wherein each base pair is associated with a unique 2-bit identifier (e.g., A=00, T=01, G=10, and C=11). In other embodiments, a 1-bit coding scheme may be used wherein two base pairs are associated with each unique 1-bit identifier (e.g., A and T may be encoded as 0, while C and G may be encoded as 1, among other possibilities). A 1-bit coding scheme may be advantageous, for example, in performing a rapid approximate candidate selection process. In such a scheme, while an exact candidate selection will not be accomplished, roughly half of the candidate locations may be ruled out for candidate selection, significantly speeding up the computational time required for a subsequent candidate selection process using a 2-bit coding scheme.

Once a coding scheme has been selected, the reference genome may be translated into a continuous series of bits based on the coding scheme. For example, if the reference genome comprises N base pairs and a 2-bit coding scheme is being used, the reference genome will be translated into a string of bits of length 2N. The encoded reference genome may further comprise chromosome separator markers, header fields, etc., as desired.

At 402, a set $L=\{l_1, l_2, l_3, \ldots, l_{Lmax}\}$ of base pair lengths may be selected. The elements of the vector L represent the lengths associated with the sequential levels of the index table. For example, $l_1$ is the length of the sequence associated with the first level entries, $l_2$ is the length of the sequence associated with the second level entries, and so on. For example, in FIG. 2, which shows sequentially increased segments of a DNA strand, the length $l_1$ may correspond to the section labelled 'initial'. The section labelled '$1^{st}$ ext' may correspond to the length $l_2$, and the section labelled '$2^{nd}$ ext' may correspond to the length $l_3$, and so on.

The set L may be selected to improve computational time and/or accuracy of the index table construction process and/or the short read alignment process. In some exemplary embodiments, the first length $l_1$ may be selected such that $4^{\wedge}(l_1) < N$. This may prove advantageous, for example, by ensuring that most of the base pair sequences of length $l_1$ will (statistically) occur in at least one location in the reference genome, hence reducing the computational time devoted to fruitless searches. In some exemplary embodiments, the sum of the elements of L, which we may refer to as $L_{total}$ may be selected such that $4^{\wedge}(L_{total}) \gg N$. In this case, a random string of bases with a length equal $L_{total}$ will statistically occur in a random string of N bases with negligible probability. For example, the longest human chromosome is approximately 250 million bases long. There are $4^{20} \approx 1$ trillion different strings of 20 base pairs, so that setting $L_{total}=20$ would result in a 0.025% probability of any particular 20 base pair string occurring in a random 250 million base pair string. Modestly increasing $L_{total}$ to 25 reduces this probability by a factor of 45=1024 to 0.000022%, so that for any physically relevant value of N, the likelihood of random statistical concurrence may be easily reduced to a negligible magnitude. This may be advantageous by, for example, reducing the likelihood that a SR is matched to a location in the reference genome because of a random correlation, and thereby increasing the chance of the match being indicative of an underlying biological relationship between the SR and the matched location in the reference genome. In other exemplary embodiments, the set L may be determined empirically to improve (or possibly optimize) computational parameters and/or accuracy of the table construction process and/or the short read alignment process.

In the present embodiment, the term length is used to refer to the linear extent of a sequence of base pairs. However, in other embodiments it may be appreciated that 'length' may more generally indicate any size metric related to a collection of data. For example, 'length' may be generalized to indicate the dimensions of a multi-dimensional array, a number of pixels, e.g., an array (4×4, etc.) of pixels, etc.

At 404, a set $C_{th}=\{th_1, th_2, th_3, \ldots, th_{Lmax-1}\}$ of count thresholds may be selected. The elements of the vector $C_{th}$ represent the thresholds associated with respective levels of the index table. In other words, the elements of the vector $C_{th}$ represent the thresholds that are used in the matching criteria applied at each respective level of the index table.

The set $C_{th}$ may be selected to improve (or possibly optimize) computational time and/or accuracy of the index table construction process and/or the short read alignment process. The improvement may be based on statistical features of the reference genome, or the improvement may be empirically determined, in various embodiments. As will be seen below, the table construction algorithm may proceed by iteratively constructing an adaptively branched tree. In some embodiments, the count thresholds may be adaptively determined for each branch of the tree. For example, an initial count threshold $th_1$ may be set, and the initial count threshold may be adaptively adjusted each time the tree branches, wherein the adaptive adjustment is based on the number of new branches formed during that iteration.

At 406, a preferably exhaustive list of possible subsequences having a first length is created. More specifically, an ordered list $M_1$ of each possible string of base pairs of length $l_1$ is constructed, wherein each possible string of base pairs of length $l_1$ is likewise translated into a string of bits using the same coding scheme used for the reference genome. The list may be ordered in binary numerical order (i.e., each string of base pairs may be converted to a binary number, and these numbers may be ordered in $M_1$ in ascending numerical order). For each string in this ordered list, the algorithm may be configured to search the reference genome for matching strings. The algorithm may be further configured to store the locations of the matching strings in the reference genome and the number of matching strings found as an entry in a data structure, wherein the entries for each of the strings in the first ordered list are stored in the same order as they occur in the first ordered list. These entries in the data structure may collectively comprise a first level of the index table.

In some embodiments, the algorithm may be further configured to construct a second level of the index table. At 416, a second ordered list, $M_2$, may be constructed of every possible string of base pairs of length $l_2$, wherein every possible string of base pairs of length $l_2$ is likewise translated into a string of bits using the same coding scheme used for the reference genome, and the list is ordered in binary numerical order.

At 408, for each $i^{th}$ entry of the first level of the index table, the algorithm may compare the number of matching locations stored in the $i^{th}$ entry with the first count threshold $th_1$.

At 410, if the number of matching locations stored in the $i^{th}$ entry does not exceed $th_1$, the algorithm may not construct a second level entry from the $i^{th}$ entry, and may store a STOP instruction associated with the $i^{th}$ entry in the data structure. This may cause the respective entry to become a terminal entry in the index table.

At 416, if the number of matching locations found in the $i^{th}$ entry exceeds $th_1$, the algorithm may, for each entry $M_2(j)$ in $M_2$, search the reference genome at each respective location stored in the $i^{th}$ entry and check whether the $l_2$ base pairs, starting at a distance of $l_1$ beyond each respective location, match $M_2(j)$. For each entry $M_2(j)$ for which this search is performed, the algorithm may store the locations wherein a match for $M_2(j)$ was found, as well as the number of matches found for $M_2(j)$ as an entry in the data structure, wherein the entries for each of the strings in the second ordered list are stored in the same order as they occur in the second ordered list. These entries may collectively comprise the second level of the index table.

In some embodiments, a third and all subsequent levels of the index table may be constructed in an iterative manner. It may be appreciated that the third level may be constructed similarly to the second level, with the following adjustments. All instances of the subscript '1' and the word 'first' in the previous paragraph may be replaced by '2' and 'second', respectively. All instances of the subscript '2' and the word 'second' in the previous paragraph may be replaced by '3' and 'third', respectively. Comparable adjustments may be made for each subsequent level of the hierarchical index table up until the Lmax level. Additionally, during construction of the third level, when checking whether each entry $M_3(j)$ of $M_3$ matches the reference genome at each respective location stored in each $i^{th}$ entry of the second level of the index, the algorithm should start at a distance of $l_1+l_2$ beyond each respective location. Subsequent levels n of the hierarchical index table would start at a distance of $l_1+l_2+\ldots+l_{n-1}$ beyond each respective location when determining whether $M_n(j)$ matches the reference genome.

At each iteration, at 418, it may be determined whether j>Lmax. If j is not greater than Lmax, the algorithm may return to 408 and create a subsequent level of the index table. If j is determined to be greater than Lmax, the algorithm may end at 420.

It may be appreciated that, during the construction of a $j^{th}$ level of the index table, if the number of matching locations found at each entry of the $(j-1)^{th}$ level does not exceed the $(j-1)^{th}$ threshold, all entries of the $(j-1)^{th}$ level may be associated with STOP instructions at 412, and the construction of the index table may conclude at 414 without proceeding to subsequent levels.

It may be further appreciated that the present invention comprises selectively constructing the hierarchical entries of the index table, such that entries are only constructed for sequences of base pairs (bp) that actually occur in the reference genome. The number of possible base pair sequences for a string of base pairs grows exponentially with the length of the string, so that an exhaustive index table with entries for all possible strings becomes prohibitively large for even a modest string length of 25 base pairs ($4^{25} \approx 1$ quadrillion entries). Most genomes contain a far, far smaller subset of all possible sequences of base pairs, which cannot be larger than the length of the genome. Selectively constructing the hierarchical entries limits the number of entries at each level to the length of the reference genome, or 3.2 billion for the case of the human genome.

Actual genomes have many, many repeated sequences, which reduces the number of entries at the first level of the hierarchy. For the human genome the most common repeated sequence is called "LINE-I"; and it is between 1000 and 6000 bp in length, and there may be 100000 copies of it, accounting for up to 14.6% of the 3.2 billion bp in the whole genome.

In some embodiments, when an entry is stored in a level of the hierarchical index table, the algorithm may be configured to pass the locations stored in the corresponding entry of the previous level of the index table, so that these locations are deleted from the corresponding entry of the previous level (the number of locations will still be stored in the corresponding entry of the previous level). In these embodiments, the locations in the reference genome will only be stored in the terminal entry of each 'branch' of the index 'tree'. Since the index table may have a very large number of branches, this may significantly reduce the size of the index table, which may reduce computational overhead.

In some embodiments, the index table may be separated, during the construction process or via post-processing, into two data structures, wherein the data indicating the number of locations associated with each entry and the data indicating the locations in the reference genome associated with each entry are each stored in a separate data structure.

The entries of each level of the index table may additionally store links to related entries at subsequent levels of the index table. For example, if a respective entry at level n is not a terminal entry, it may comprise a pointer that indicates the location of entries at the n+1 level that are derived from the respective entry. The respective entry may further store the length $l_{n+1}$ that is associated with the subsequent level of the index table. The pointer and length information may, for example, allow a search of the index table to be quickly directed to the entry in the index table that corresponds to any particular search sequence.

Figure 5:
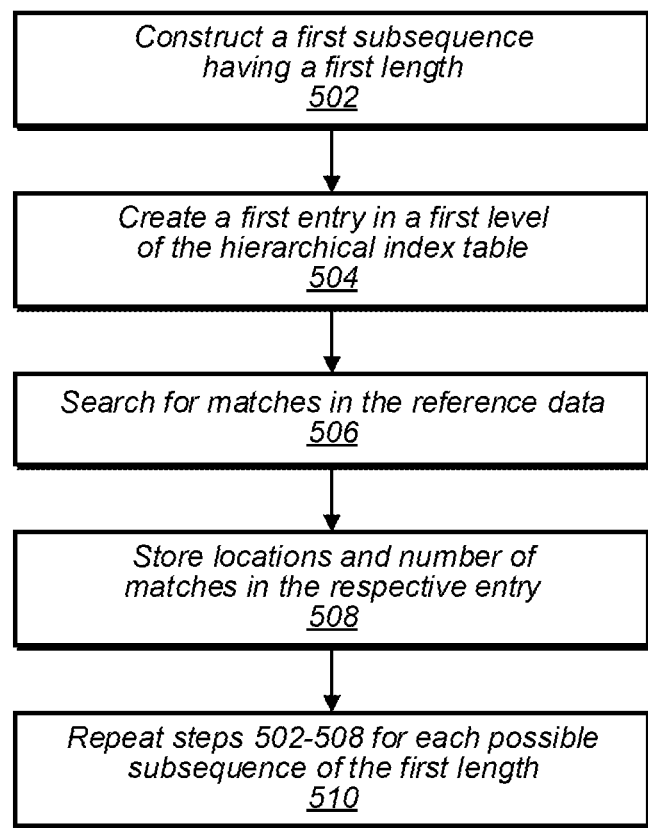
FIG. 5 is a flowchart diagram illustrating a method for constructing a first level of a hierarchical index table, in some embodiments.

FIG. 5—Construction of a First Level of a Hierarchical Index Table

FIG. 5 is a flowchart showing an exemplary process by which the first level of a hierarchical index table may be constructed from reference data.

At 502, a first subsequence having a first length may be constructed. The first length may be selected such that any random subsequence of the first length is statistically likely to occur at least once in the reference data. The subsequence may be encoded numerically, e.g., in binary. In exemplary embodiments, the subsequence may comprise a string of DNA base pairs, which may be encoded in a 1-bit or 2-bit binary format. The first subsequence may be constructed such that it has the lowest possible numerical magnitude when it is encoded numerically. For example, in the case of 2-bit encoding of a string of DNA base pairs, the first subsequence may be a string of '0's that is twice as long as the first length.

At 504, a first entry in a first level of a hierarchical index table is created. The first entry is associated with the first subsequence.

At 506, a search is made in the reference data for matches of the first subsequence. The search may be exhaustive, whereby it searches the entire reference data for matches. The search may record both the number of matches and each of their locations in the reference data.

At 508, the number of matches and each of their locations may be stored in the first entry in the first level of the hierarchical index table. In some embodiments, the number of matches may be stored in a first data structure, while the locations of the matches may be stored in a second data structure, wherein the first data structure further comprises a pointer to the respective entry in the second data structure.

At 510, each of steps 502-508 may be repeated for each subsequence of the first length. For example, if the subsequence is a string of DNA base pairs, steps 502-508 may be repeated for every combination of base pairs of the first length. Each sequential subsequence may be selected so that the numerically encoded subsequences occur in ascending numerical order. For example, in the example given above for step S102 in which a 2-bit (binary) encoding scheme for a string of DNA base pairs, the second subsequence may be selected to be '000 . . . 00010', where the ellipsis comprise an appropriate number of '0's such that the length of the binary string is twice the first length. In this case, the entries in the first level of the index table may be created in ascending numerical order, such that the location in the index table of an entry corresponding to any given subsequence of the first length may be trivially ascertained.

Figure 6:
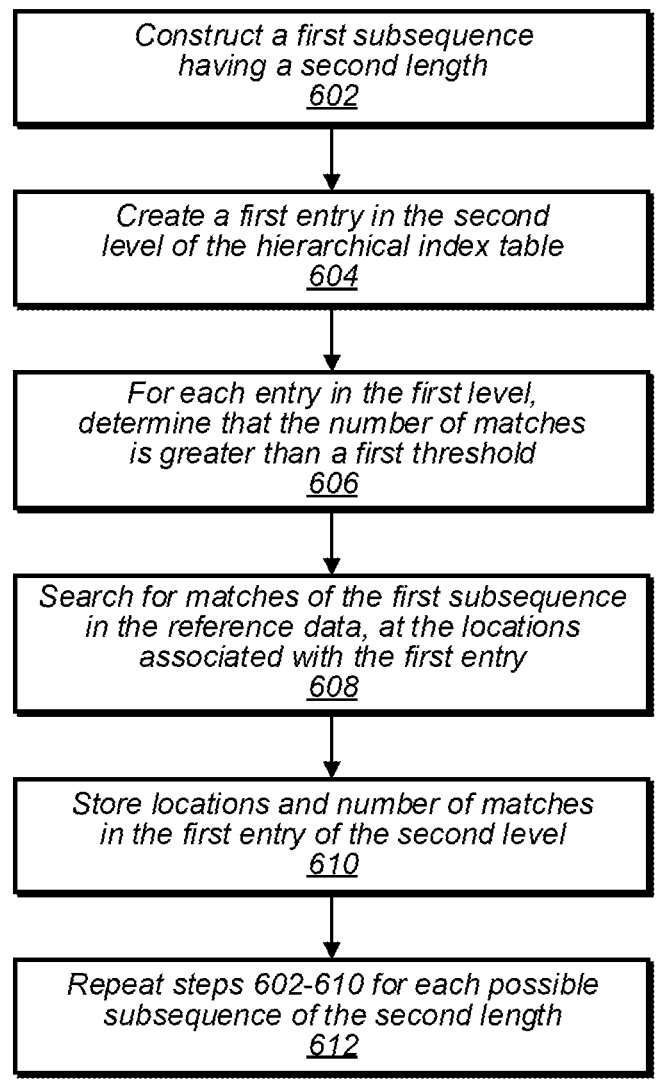
FIG. 6 is a flowchart diagram illustrating a method for constructing a second level of a hierarchical index table, in some embodiments.

FIG. 6—Construction of a Second Level of a Hierarchical Index Table.

FIG. 6 is a flowchart of an exemplary process by which a second level of the hierarchical index table may be constructed.

At 602, a first subsequence having a second length may be constructed. The second length may be determined empirically, or based on statistical parameters of the reference data, in such a way as to improve computational parameters and/or accuracy of the process of mapping the data pattern to the reference data. Similar to the first subsequence of the first length, the first subsequence having a second length may be encoded numerically, and may be selected to have the smallest numerical magnitude.

At 604, a first entry in the second level of the hierarchical index table may be created. The first entry may be associated with the first subsequence.

At 606, for each entry in the first level of the hierarchical index table, it may be determined that the number of matches in that entry is greater than a first threshold. The first threshold may be determined empirically, or based on statistical parameters of the reference data, in such a way as to improve computational parameters and/or accuracy of the process of mapping the data pattern to the reference data.

At 608, a search is made for matches of the first subsequence in the reference data. At 608, the search is not an exhaustive search of the entire reference data. Rather, the search is performed only at locations in the reference data that are associated with the respective entry in the first level of the index table. In particular, for each matched location in the reference genome for the respective entry in the first level referenced at 606, a search is made at that location plus the first length. In other words, a search is made whether each match of the first length additionally matches for the subsequent second length.

At 610, the number of matches and the locations of each match found at 608 are stored in the first entry of the second level of the index table. In some embodiments, the number of matches may be stored in a first data structure, while the locations of the matches may be stored in a second data structure, wherein the first data structure further comprises a pointer to the respective entry in the second data structure.

At 612, each of steps 602-610 may be repeated for each possible subsequence of the second length. For example, if the subsequence is a string of DNA base pairs, steps 602-610 may be repeated for every combination of base pairs of the second length. Each sequential subsequence may be selected so that the numerically encoded subsequences occur in ascending numerical order. In this case, a set of entries in the second level will be created corresponding to each of the entries in the first level for which the first threshold was determined to be exceeded at 606, and each of these sets will be internally ordered in ascending numerical order, such that the location in the index table of an entry corresponding to any given subsequence of the second length and associated with any given subsequence of the first length may be trivially ascertained.

Exemplary Candidate Selection Processes

Herein we detail an exemplary algorithm for performing candidate selection for a SR using a hierarchical index table. Initially, a footprint F of length K of the SR may be selected for comparison to the reference genome. The length K may be selected, in some embodiments, such that the probability of a mismatch or indel within a length K is less than a predetermined threshold. In some embodiments, the length K may be selected to be the first entry in L, i.e., $l_1$.

In some embodiments, the length K may be iteratively adapted to improve computational requirements of the DNA alignment process. For example, an initial length K may be selected and the respective footprint may be looked up in the index table. If the number of candidate locations at the looked up entry is above a predetermined threshold number of locations, the length K may be incrementally increased by a predetermined length and the lengthened footprint may be looked up in the index table. The new looked-up entry may contain a number of locations greater than the predetermined threshold number of locations, and the length K may be again incrementally increased by a predetermined length and the lengthened footprint may be looked up in the index table, and so on. This process may be iteratively repeated until the number of candidate locations is found to not exceed the predetermined threshold number of locations. Candidate evaluation is a computationally intensive task, and reducing the number of candidate locations to a manageable amount may significantly reduce the computational burden of the DNA alignment process.

In some embodiments, the predetermined threshold number of locations may be comprised in the set of thresholds $C_{th}$ that was used in the construction of the hierarchical index table. For example, the candidate selection process may be configured to return the matched locations in the reference genome only if the entry in the index table corresponding to the footprint is a terminal entry in the index table, i.e., if the entry is associated with a STOP command. If the entry associated with the footprint is not associated with a STOP command, the candidate selection process may be configured to increase the length of the footprint by the length associated with the subsequent level of the index table, and look up the corresponding entry in the index table for the lengthened footprint, in some embodiments.

FIG. 7—Example Implementation of Performing Search with a Hierarchical Index Table An example embodiment of the process of incrementally increasing K is illustrated in FIG. 7, which shows an example search algorithm applied to the SR of FIG. 2. In FIG. 7, the initial length K is designated as 'initial', and the algorithm is directed to a first entry in amt_loc table 0 in the index table. The 'f' field in the amt_loc table 0 describes whether a STOP command is associated (S) or is not associated (/) with that entry. It is found that the first entry is not a terminal entry in the index table, upon which the length K is incrementally increased by an amount "$1^{st}$ ext" and the algorithm is directed to a new corresponding entry in amt_loc table 1. Here it is again found that the new corresponding entry is likewise not a terminal entry, and the length K is subsequently increased again by an amount "$2^{nd}$ ext" and the algorithm is directed to another corresponding entry in amt_loc table 2. Here it is found that the corresponding entry is a terminal entry, so that the algorithm is directed to a particular row in bas_loc table 2, where the locations in the genome (ppp in FIG. 7) that match the extended string F are read off starting from the first entry in bas_loc table 2 that corresponds to the extended string F.

It may be appreciated that tables amt_loc table 0, amt_loc table 1, and amt_loc table 2 comprise sequential levels of the hierarchical index table, according to some embodiments. It may be further appreciated that the distinction between the set of 'amt_loc' tables and 'bas_loc' tables illustrates the separation of the information regarding the number of matches found and the location of those matches into two distinct data structures, according to some embodiments.

The footprint may be selected from the beginning, from the middle, or from the end of the SR, in various embodiments. In some embodiments, separate footprints of length K may be selected from each of the beginning, the middle, and/or the end of the SR, and matches found from each footprint may be aggregated together in the candidate selection process.

In DNA alignment, it is generally necessary to consider both the forward and "reverse-complement" directions of the SR with respect to the reference genome. The reverse-complement direction is the SR, read backwards, and translating all A bases to T, T bases to A, C bases to G, and G bases to C. For example, the following SR segment is associated with the following reverse-complement segment:

```
ACGTCTGATTGACAAACTGATGCA    original
TGCATCAGTTTGTCAATCAGACGT    reverse-complement
```

Therefore, footprints may be selected in both directions to determine candidate locations. In some embodiments, it may be further advantageous to perform candidate selection using a reverse footprint (not complemented), and/or a complement footprint (not reversed).

In some embodiments, a validity or quality score may be assigned to each base pair in the SR, wherein the validity or quality score is related to the expected reliability of the base pair in the SR. For example, a base pair in the SR that was read with high confidence or fidelity may be assigned a higher validity or quality score. In these embodiments, the footprint F may be preferentially selected from a portion of the SR that comprises the highest aggregated quality score of the base pairs located within F. In other embodiments, the presence of a base pair in the footprint with a low quality score may cause the search to split at that base pair. For example, if the $5^{th}$ base pair of a footprint is designated as a C with a low quality score, the candidate search may proceed with 4 independent searches, wherein the $5^{th}$ base pair is substituted as each of A, C, G, and T for the 4 independent searches. The matches found for each of these 4 searches may then be aggregated together in the final output of the search process. It may be understood that this embodiment may be extended to the case of multiple base pairs being associated with low quality scores.

If an exact match between F and the reference genome is sought, the algorithm may be configured to use the stored links to entries in subsequent levels of the index table to look up the entry in the index table that corresponds to F. The locations contained in the entry corresponding to F may then be read off and subsequently used for candidate evaluation. Many present DNA alignment algorithms are required to perform binary or other computationally intensive searches to find the entry in the reference index table that matches F. The systematic organization of the index table in the present invention may significantly reduce computational effort and latency, since only pointer information of the relevant entries of the index table, rather than the bulk of the information stored in the index table, needs to be read and processed in order to find the entry corresponding to F in the index table.

In some embodiments, it may be desirable to find candidate locations in the reference genome that approximately match F. For example, it may be desirable to store all locations in the reference genome that have fewer than x mismatches with F. In these cases, the algorithm for performing candidate selection may be configured as follows.

The algorithm may initially compare the first $l_1$ base pairs of F with each entry in $M_1$. The algorithm may store each entry in $M_1$ that contains fewer than x mismatches with F. For each stored entry of length $l_1$, the algorithm may append each string of length $l_2$ in the second level of the index table and compare the resulting string to the first $l_1+l_2$ base pairs of F. For each such comparison that results in fewer than x mismatches, the algorithm may proceed analogously to the third and subsequent levels of the index table. This process may be iterated until a STOP instruction is encountered for a particular entry in a particular level of the index table, or until the number of mismatches found exceeds x. The locations associated with each entry in the index table that are associated with an encountered STOP instruction may then be read off and used for candidate evaluation.

In some embodiments, the algorithm may be configured to use a running sum of the number of mismatches between the reference genome and F while determining an approximate match for candidate selection. In this case the algorithm may be configured to perform similarly to the previous paragraph, but with several modifications. The algorithm may initially compare the first $l_1$ base pairs of F with each entry in $M_1$. The algorithm may store each entry in $M_1$ that contains fewer than x mismatches with F, and may store a running sum of the number of mismatches recorded for each entry stored. For each stored entry of length $l_1$, the algorithm may compare each string of length $l_2$ to the subsequent $l_2$ base pairs of F, and add the number of mismatches found to the running sums. For each running sum that is less than x, the algorithm may proceed analogously to the third and subsequent levels of the index table. This process may be iterated until a STOP instruction is encountered for a particular entry in a particular level of the index table, or until the running sum is found to exceed x (whichever occurs first). The locations associated with each entry in the index table that are associated with an encountered STOP instruction may then be read off and used for candidate evaluation.

In some embodiments, it may be appreciated that the preceding candidate selection algorithms lend themselves to expeditious parallelization. For example, since the candidate selection process for each SR is programmatically independent and uses a common index table, candidate selection algorithms for many SRs may be performed simultaneously, significantly speeding up computational performance.

Figure 8:
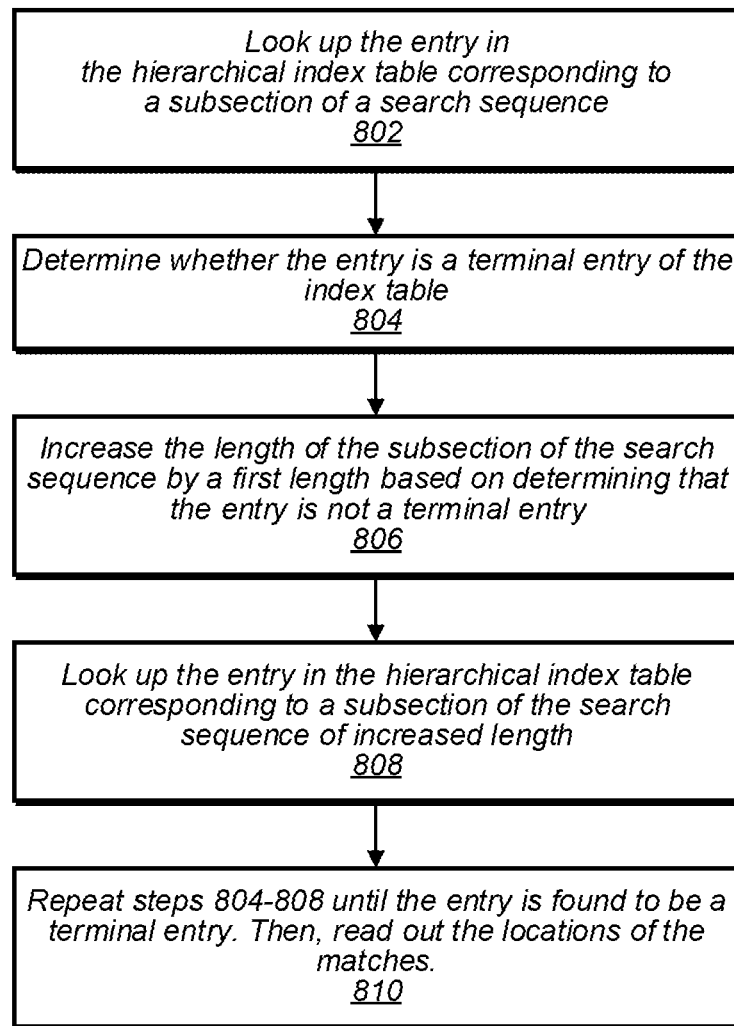
FIG. 8 is a flowchart diagram illustrating a method for searching reference data for matches of a subsection of a search sequence using a hierarchical index table, in some embodiments.

FIG. 8—Matching a Search Sequence to Reference Data

FIG. 8 is a flowchart showing an exemplary process by which a search sequence is matched to reference data using a hierarchical index table.

At 802, a subsection of a search sequence is looked up in the hierarchical index table. The length of the subsection of the search sequence may be selected empirically or based on statistical characterizations of the hierarchical index table to improve computational parameters of the matching process. Because of the ordered numerical structure of the index table, the lookup process may be quickly directed to the entry in the index table that corresponds to the subsection of the search sequence. This entry may then be read to determine information contained in the entry.

At 804, it may be determined whether the entry found in 802 is a terminal entry of the index table. A terminal entry may be an entry that is associated with a STOP command, i.e., a terminal entry may not be associated with any entries in higher levels of the index table.

At 806, the length of the subsection of the search sequence may be increased by a first length based on determining that the entry is not a terminal entry. The first length may be selected to equal the length associated with the subsequent level of the index table.

At 808, a search is made of the reference data using the hierarchical index table for matches of the subsection of the search sequence of increased length. 808 may proceed analogously to 802, but with a lengthened subsection of the search sequence.

At 810, steps 804-808 may be iteratively repeated until it is determined that the looked-up entry is a terminal entry of the index table. Each iteration of steps 804-808 may be executed with unique first lengths, as desired. If the looked-up entry is found to be a terminal entry of the index table, the matching process may read the locations of the matches found from the hierarchical index table and proceed to candidate evaluation.

Candidate Evaluation

Once a set of candidate locations have been selected for a particular SR, a candidate evaluation process may be implemented to compare the entirety of the SR to the reference genome. In the candidate evaluation process, misfits (where a base is different than in the reference genome) may be allowed, and in fact are extremely interesting biologically. Generally, a valid alignment is one where the number of misfits between the SR and the reference genome at the aligned position are within acceptable limits, i.e., the number of misfits may be greater than zero but less than some predetermined threshold. In this case the characterization and location of the misfits in an alignment may be an important output of the computation.

Misfits may take the form of substitutions, wherein one base pair is substituted for another base pair. Misfits may also be insertions, where the SR has 1 or more bases inserted which do not occur in the reference genome at the aligned position. Likewise, misfits may be deletions, where one or more bases are missing from the SR but are present in the reference genome. Insertions and deletions are collectively referred to as 'indels'.

For example, the 24-base SR ACGTCTGATTGACAAACTGATGCA could have these types of alignments:

```
Ref:      ACGTCTGATTGACAAACTGATGCA
SR:       ACGTCTGATTGACAAACTGATGCA
misfits:  ........................   0 misfits, an "indentical" match Ref:      AGGTCAGATTGACAAACTGATGCA
SR:       ACGTCTGATTGACAAACTGATGCA
misfits:  .!....!.................   2 misfits in an "exact" match Ref:      ACGTC___TGATTGACAAACTGATGCA
SR:       ACGTCGGATGATTGACAAACTGATGCA
misfits:  .....!!!...................   3 misfits from an insertion Ref:      ACGTCTGATTTACGGACAAACTGATGCA
SR:       ACGTCTGATT____GACAAACTGATGCA
misfits:  ..........!!!!..............  4 misfits from a deletion
```

Combinations of the above can occur as well, for example:

```
Ref:      ACGTATGATTTACGGACAAACTGCGGCA
SR:       ACGTCTGATT____GACAAACTGATGCA
misfits:  ....!.....!!!!.........!!...  6 total
                                       misfits
```

Locating misfits in an exact match is relatively easy: one only needs to compare the bases one by one. Locating insertions and/or deletions (collectively, indels) requires much more processing, and therefore a more sophisticated approach.

Identifying SRs Containing Likely Indels

As a first step, it may be determined whether a SR is likely to contain an indel relative to a location in the genome that was identified through candidate selection. This step will proceed differently depending on whether F was selected from the beginning, the middle, or the end of the SR. In the case where F was selected from the beginning of the SR, a running sum of the number of misfits between the SR and the reference genome, from the last position to the first position in the SR, may be recorded. If an indel is present in the SR, base pairs located farther from the beginning of the SR than the location of the indel may contain a mismatch with the reference genome ¾ of the time on average (because there are 4 base pairs and an offset would cause them to randomly match with a 25% chance). Starting from the end of the SR, a running average of the number of mismatches per base pair may be recorded. If the running average is within a predetermined threshold of ¾ for a predetermined number of subsequent base pairs, it may be determined that an indel is likely present. It is appreciated that DNA sequences do not comprise random sequences of base pairs, and other embodiments may use a ratio of average mismatches other than ¾. For example, a ratio may be determined empirically, or from statistical considerations of the DNA sequence.

In the case where F was selected from the end of the SR, a comparable process may be used to determine the likely presence of an indel. In this case, starting from the beginning of the SR, a running average of the number of mismatches per base pair may be recorded. If the running average is within a predetermined threshold of ¾ for a predetermined number of subsequent base pairs, it may be determined that an indel is likely present.

In some embodiments, the predetermined threshold and the predetermined number of subsequent base pairs may be adapted to improve run time and accuracy of the indel identification process, as desired.

In some embodiments, the likely presence of an indel may be ascertained by calculating a gradient change of misfit frequency using a running sum of misfits. For example, an average misfit frequency may be calculated using a running sum of misfits from an end of a SR. If the average misfit frequency is found to change at a particular position in the SR, wherein the change is found to be greater than a predetermined threshold magnitude, and the change is furthermore found to persist for a predetermined extent of base pairs, it may be determined that an indel is likely to be present in the SR. A likely misfit may be analogously identified by calculating a gradient of the misfit frequency over the length of the SR, and considering an indel to likely be present if the gradient spikes above a predetermined threshold within the extent of the SR.

Characterizing and Locating Indels

One embodiment of the present techniques uses a 4-step approach to evaluating a candidate position for indels:

Step 1: Lo-end and Hi-end misfits
Step 2: Length and Type
Step 3: Error sums
Step 4: Indel position This methodology may result in an indel of 4 types being found: deletion using a lo-end anchor, insertion using a lo-end anchor, deletion using a hi-end anchor, and insertion using a hi-end anchor. One of these types, deletion using a hi-end anchor, is discussed below with respect to an example. Note that the other exemplary cases described herein are similar.

The terms "lo-end" and "hi-end" refer to respective ends of the SR. For example, lo-end bases are those at the lo-end of the SR. Using a lo-end anchor position means to hold the lo-end at a constant position, and vary the hi-end position as if bases were deleted or inserted into the middle of the SR. Likewise, using a hi-end anchor position means to hold the hi-end at a constant position, and vary the lo-end position as if bases were deleted or inserted into the middle of the SR.

Step 1: Selection of Lo-End or Hi-End Anchors

In this step, a detector size of S bases may be used to check the lo-end and hi-end of the SR. The number of misfits between the lo-end S bases of the SR and the lo-end S bases of the reference genome at the SR candidate alignment position may be counted; these are the lo-end misfits. Likewise, the number of misfits between the hi-end S bases of the SR and the hi-end S bases of the reference genome at the SR candidate alignment position may be counted; these are the hi-end misfits. Note that S can be a tunable parameter; one embodiment uses 24 bases.

If the number of lo-end misfits is greater than a threshold U and the hi-end misfits is less than a threshold M, use of the hi-end anchor position may be indicated (advised). Likewise, if the hi-end misfits is greater than the threshold U and the lo-end misfits is less than the threshold M, use of the lo-end anchor position may be indicated (advised). If neither of these conditions is true, indel searching for this candidate position may cease. Note that U and M are tunable parameters; one embodiment uses 4 and 6, respectively.

In some embodiments, if a candidate location was selected by comparison of a lo-end footprint to the reference genome, a lo-end anchor may be automatically selected since the lo-end is already known to be lined up appropriately with the candidate location in the reference genome. Similarly, if a candidate location was selected by comparison of a hi-end footprint to the reference genome, a hi-end anchor may be automatically selected. In cases where a footprint selected from the middle of the SR was used to select a particular candidate location, it may be advantageous to perform the anchor selection process described above. In these cases, the middle of the SR may be aligned with the candidate location, but it may be unknown whether a potential indel is present on the lo or the hi side of the SR.

Step 2: Length and Type

If an indel is suspected, the next step may determine both the length of the indel, and the type (insertion or deletion). The user may provide a maximum indel length to search for (IDIST). One embodiment performs a series of misfit counts using either the lo-end or hi-end part of the SR (opposite the anchor end), depending on where the indel is suspected to be. The counts may use B bases, and may vary the candidate position by D=[−IDIST . . . +IDIST]. Note that B is a tunable parameter; one embodiment uses a value of 8. The offset value D may be recorded which may result in the minimum number of misfits. In one embodiment:

If D=0, there is no indel, and searching stops for this candidate.

If D<0, a possible insertion is found with length=|D|.

If D>0, a possible deletion is found with length=D.

Given the length and type of the indel, the starting position should be found. This may be performed in the next two steps: Error sums and Indel position.

Step 3: Error Sums

In this step two running error sums may be computed. The first running sum may be between the SR and the reference genome at the candidate position, and the second may be between the SR and the reference genome at the (candidate+D) position; note that D may be negative for the insertion case.

Step 4: Indel Position

The final step is to locate the start of the indel. This may be performed by finding the minimum of the sum of the two count arrays, using an adjustment based on the type.

In the case of an insertion, the following may be computed (note: indices start at 1, not 0):

$$\text{sum}[i]=(\text{count2}[\text{Bases}]-\text{count2}[\text{length}+i])+\text{count1}[i],$$
$$\text{for } i \text{ in } [1 \ldots \text{Bases}-\text{length}]$$

Next, find the minimum value of sum[i], with i in [2 . . . Bases−length]. The starting position of the insertion is i.

In the case of a deletion, compute:

$$\text{sum}[i]=(\text{count2}[\text{Bases}]-\text{count2}[i])+\text{count1}[i], \text{ for } i \text{ in } [1 \ldots \text{Bases}]$$

Then find the minimum value of sum[i], with i in [2 . . . Bases]. The starting position of the deletion is i.

EXAMPLE

In the following example, each step is performed using the following SR and SR candidate position:

```
Ref:         ACGTCTGATTTACGGACAAACTGATGCA

SR:          ACGTCTGATTGACAAACTGATGCA
```

Example Step 1: Lo-End and Hi-End Misfits

Note that because a 24-base SR is used instead of the more typical 100-base SR, the detector size and thresholds are adjusted to S=6, U=1, M=2 for the purpose of these examples:

```
Ref:         ACGTCTGATTTACGGACAAACTGATGCA

SR:          ACGTCTGATTGACAAACTGATGCA
``` lo-end misfits: . . . . . . - - - - - - - - - - - - - - - - - - lo-end misfits=0 hi-end misfits: - - - - - - - - - - - - - - - - - - ! . ! ! ! . hi-end misfits=4

The lo-end misfits is 0 (ACGTCT vs. ACGTCT); the hi-end misfits is 4 (GATGCA vs. AACTGA). Since hi-end misfits >U and lo-end misfits <M [(4 >1) && (0<2)], an indel will be searched for using a lo-end anchor position.

Example Step 2: Length and Type

Because a lo-end anchor has been determined, the type and length of the indel may be determined using the hi-end bases. Note that for this example, B=8 and IDIST=4:

```
D = -4  Ref:  ----ACGTCTGATTTACGGACAAA
        SR:       ACGTCTGATTGACAAACTGATGCA
        mistits:  ---------------.!..!!!.   4 misfits at hi-end
```

```
              -continued
D = -3 Ref:   ---ACGTCTGATTTACGGACAAAC
SR:              ACGTCTGATTGACAAACTGATGCA
mistits:         ----------------!!!!!!!!    8 misfits D = -2 Ref:   --ACGTCTGATTTACGGACAAACT
SR:              ACGTCTGATTGACAAACTGATGCA
mistits:         ----------------!!!.!!.!    6 misfits D = -1 Ref:   -ACGTCTGATTTACGGACAAACTG
SR:              ACGTCTGATTGACAAACTGATGCA
mistits:         ----------------!!!.!!!!    7 misfits D =  0 Ref:   ACGTCTGATTTACGGACAAACTGA
SR:              ACGTCTGATTGACAAACTGATGCA
mistits:         -----------------.!!.!!!.   5 misfits D = +1 Ref:   CGTCTGATTTACGGACAAACTGAT
SR:              ACGTCTGATTGACAAACTGATGCA
mistits:         ----------------!!!!..!!    6 misfits D = +2 Ref:   GTCTGATTTACGGACAAACTGATG
SR:              ACGTCTGATTGACAAACTGATGCA
mistits:         ----------------!!!!!!!!    8 misfits D = +3 Ref:   TCTGATTTACGGACAAACTGATGC
SR:              ACGTCTGATTGACAAACTGATGCA
mistits:         ----------------!!!!!!!!    8 misfits D = +4 Ref:   CTGATTTACGGACAAACTGATGCA
SR:              ACGTCTGATTGACAAACTGATGCA
mistits:         --------------------....    0 misfits  <-- minimum
```

Since D is >0, a possible deletion has been found with length=+4.

Example Step 3: Error Sums

Using the deletion case mentioned above:

```
at candidate position
Ref:
ACGTCTGATTTACGGACAAACTGA

SR:
ACGTCTGATTGACAAACTGATGCA misfits:
..........!..!!..!!.!!!.

count1: <- running sum of misfits
000000000011123334556788 at candidate +4 position
Ref:
CTGATTTACGGACAAACTGATGCA

SR:
ACGTCTGATTGACAAACTGATGCA misfits:
!!.!!.!.!!..............

count2: <- running sum of misfits
122344556777777777777777
```

Example Step 4: Indel Position

Since a deletion is being searched for, the method may compute sum[i] for indices
[1 ... Bases-length], as described above.
7-count2 [i]: 6554332210000000000
count1 [i]:   0000000001112333455
sum [i]:      6554332210111233455

The minimum occurs at index i=10. This means the number of bases before the indel is 10, followed by a 4-base deletion (from step 2), followed by (bases—10) matching bases after the indel. The Compact Idiosyncratic Gapped Alignment Report (CIGAR) value may then be 10M4D14M, where a CIGAR string is a sequence of base lengths and the associated operation, and is used to indicate items such as which bases align (either a match/mismatch) with the reference, which are deleted from the reference, and which are insertions that are not in the reference.

Figure 9:
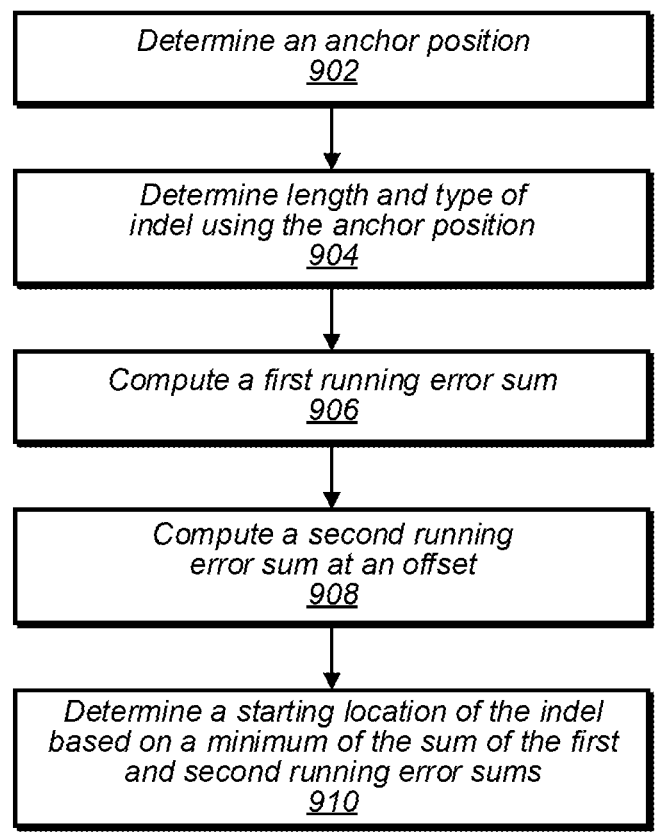
FIG. 9 is a flowchart diagram illustrating a method characterizing and locating an indel, in some embodiments.

FIG. 9—Method for Characterizing and Locating an Indel

FIG. 9 is a flowchart showing an exemplary method for characterizing and locating an indel. The method of FIG. 9 may be performed on each match found at the conclusion of the methods shown in FIG. 8.

At 902, an anchor position for the search sequence is determined. The anchor position may be determined to be at the hi-end or the lo-end of the search sequence. The anchor position may be determined by comparing a first length of positions from each of the hi-end and the lo-end to the reference data, and selecting the anchor position at the end with fewer mismatches.

At 904, a length and type of an indel may be determined using the anchor position. For example, if a lo-end anchor was determined at 702, mismatches may be counted from the hi-end of the search sequence with various offsets in place, and an offset may be selected which results in a minimum number of mismatches.

At 906, a first running error sum may be computed. The first running error sum may be computed from the anchor position. For a lo-end anchor, the running error sum may proceed forward from the lo-end anchor position. For a hi-end anchor, the running error sum may proceed in reverse from the hi-end anchor position.

At 908, a second running error sum at an offset may be computed. The offset may be determined to be the offset selected at 704. The second running error sum may likewise be computed from the anchor position.

At 910, a starting location of the indel may be determined based on a minimum of the sum of the first and second running error sums. For example, the first and second running sums may be added together. The first running error sum is constructed such that it will likely not produce mismatches for the region of the search sequence between the anchor position and the location of the indel. The second running error sum is constructed such that it will likely not produce mismatches for the region of the search sequence between the end opposite the anchor position and the location of the indel. By summing the first and second running sums together, the location with the lowest number of mismatches may be determined to be the location of the indel.

Other embodiments of the invention are represented in the following numbered paragraphs:

1. A method for matching a subsection of a search sequence to reference data, the method comprising:
    storing a hierarchical index table that is derived from the reference data, wherein the hierarchical index table comprises a plurality of entries at a plurality of hierarchical levels,
    increasing the length of the subsection of the search sequence based on determining that a first entry in the hierarchical index table associated with the search sequence is not a terminal entry of the index table, and
    looking up a second entry in the hierarchical index table that matches the subsection of the search sequence of increased length based on determining that the first entry is not a terminal entry of the hierarchical index table.

2. A method for evaluating a match of a search sequence to reference data, the method comprising:
    determining misfits between the search sequence and the reference data based on identifying base errors between the search sequence and the reference data,
    determining at least one indel in the search sequence, comprising:
    determining an anchor position in the search sequence based on a number of lo-end and hi-end misfits of the search sequence;
    determining length and type of the at least one indel using the anchor position;
    determining a starting position of the at least one indel, comprising:
    computing a first running error sum between the search sequence and the reference data at the match location;
    computing a second running error sum between the search sequence and the reference data at an offset from the match location, wherein the offset is based on the type and length of the at least one indel; and
    determining a starting location of the at least one indel based on a minimum of the first and second running error sums.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A multiprocessor array (MPA) comprising interspersed processors and communication elements coupled to at least one non-transitory computer-readable memory medium, wherein the at least one non-transitory computer-readable memory medium comprises program instructions executable by the MPA to:
- determine a length and a type of an indel in a search sequence using an anchor position in the search sequence, wherein the search sequence is matched to reference data at a match location;
- determine a starting position of the indel, wherein, in determining the starting position of the indel, the program instructions are executable to cause the MPA to:
  - compute a first running error sum between the search sequence and the reference data matched at the match location; and
  - compute a second running error sum between the search sequence and the reference data matched at an offset from the match location, wherein the offset is based on the type and length of the indel;
  - determine the starting position of the indel to correspond to a minimum of the second running error sum subtracted from the first running error sum; and
- store the length, size, and starting position of the indel in the non-transitory computer-readable memory medium.

2. The MPA of claim 1, wherein the program instructions are further executable to cause the MPA to:
- select the anchor position in the search sequence, wherein, in selecting the anchor position in the search sequence, the program instructions are executable to cause the MPA to:
  - determine a first number of mismatches at a low end of the search sequence and a second number of mismatches at a high end of the search sequence; and
  - select the anchor position to be the low end or the high end based on a comparison of the first and second numbers.

3. The MPA of claim 1,
wherein, in determining the length and the type of the indel using the anchor position, the program instructions are executable to cause the MPA to:
- for each of a plurality of offsets from the match location:
  - determine a respective number of mismatches between the search sequence and the reference data within a predetermined number of locations from an opposite end of the search sequence from the anchor position;
- determine the length of the indel to correspond to a magnitude of a first offset of the plurality of offsets corresponding to a smallest number of mismatches; and
- determine the type of the indel to be an insertion when the first offset is negative and a deletion when the first offset is positive.

4. The MPA of claim 1,
wherein the first and second running error sums are computed starting from the anchor position.

5. The MPA of claim 1, wherein the program instructions are further executable to cause the MPA to:
- match the search sequence to the reference data using a hierarchical index table.

6. The MPA of claim 1,
wherein the reference data comprises a reference genome, and
wherein the search sequence comprises a short read of a sample genome.

7. The MPA of claim 1, wherein the program instructions are further executable to cause the MPA to:
- determine a running average of a number of mismatches of the search sequence to the reference data from a first end of the search sequence for a predetermined number of locations; and
- determine whether the running average is within a predetermined threshold of a first ratio, wherein determining the length, type and starting position of the indel is performed responsive to a determination that the running average is within the predetermined threshold of the first ratio.

8. The MPA of claim 7,
wherein the reference data comprises a reference genome,
wherein the search sequence comprises a short read of a sample genome, and
wherein the first ratio is ¾.

9. A non-transitory computer-readable memory medium comprising program instructions for characterizing an indel in a search sequence, wherein the program instructions are executable to:
- determine a length and a type of the indel using an anchor position in the search sequence, wherein the search sequence is matched to reference data at a match location;

determine a starting position of the indel, wherein, in determining the starting position of the indel, the program instructions are executable to:
compute a first running error sum between the search sequence and the reference data matched at the match location; and
compute a second running error sum between the search sequence and the reference data matched at an offset from the match location, wherein the offset is based on the type and length of the indel;
determine the starting position of the indel to correspond to a minimum of the second running error sum subtracted from the first running error sum; and
store the length, size, and starting position of the indel in the non-transitory computer-readable memory medium.

10. The non-transitory computer-readable memory medium of claim 9, wherein the program instructions are further executable to:
select the anchor position in the search sequence, wherein, in selecting the anchor position in the search sequence, the program instructions are executable to:
determine a first number of mismatches at a low end of the search sequence and a second number of mismatches at a high end of the search sequence; and
select the anchor position to be the low end or the high end based on a comparison of the first and second numbers.

11. The non-transitory computer-readable memory medium of claim 9,
wherein, in determining the length and the type of the indel using the anchor position, the program instructions are executable to:
for each of a plurality of offsets from the match location:
determine a respective number of mismatches between the search sequence and the reference data within a predetermined number of locations from an opposite end of the search sequence from the anchor position;
determine the length of the indel to correspond to a magnitude of a first offset of the plurality of offsets corresponding to a smallest number of mismatches; and
determine the type of the indel to be an insertion when the first offset is negative and a deletion when the first offset is positive.

12. The non-transitory computer-readable memory medium of claim 9,
wherein the first and second running error sums are computed starting from the anchor position.

13. The non-transitory computer-readable memory medium of claim 9,
wherein the reference data comprises a reference genome, and
wherein the search sequence comprises a short read of a sample genome.

14. A method for characterizing an indel in a search sequence, wherein the search sequence is matched to reference data at a match location, the method comprising:
determining a length and a type of the indel using an anchor position in the search sequence;
determining a starting position of the indel, comprising:
computing a first running error sum between the search sequence and the reference data matched at the match location; and
computing a second running error sum between the search sequence and the reference data matched at an offset from the match location, wherein the offset is based on the type and length of the indel;
determining the starting position of the indel to correspond to a minimum of the second running error sum subtracted from the first running error sum; and
storing the length, size, and starting position of the indel in a non-transitory computer-readable memory medium.

15. The method of claim 14, further comprising:
selecting the anchor position in the search sequence, comprising:
determining a first number of mismatches at a low end of the search sequence and a second number of mismatches at a high end of the search sequence; and
selecting the anchor position to be the low end or the high end based on a comparison of the first and second numbers.

16. The method of claim 14,
wherein determining the length and the type of the indel using the anchor position comprises:
for each of a plurality of offsets from the match location:
determine a respective number of mismatches between the search sequence and the reference data within a predetermined number of locations from an opposite end of the search sequence from the anchor position;
determining the length of the indel to correspond to a magnitude of a first offset of the plurality of offsets corresponding to a smallest number of mismatches; and
determining the type of the indel to be an insertion when the first offset is negative and a deletion when the first offset is positive.

17. The method of claim 14,
wherein the first and second running error sums are computed starting from the anchor position.

18. The method of claim 14, further comprising;
matching the search sequence to the reference data using a hierarchical index table.

19. The method of claim 14,
wherein the reference data comprises a reference genome, and
wherein the search sequence comprises a short read of a sample genome.

20. The method of claim 14, further comprising:
determining a running average of a number of mismatches of the search sequence to the reference data from a first end of the search sequence for a predetermined number of locations;
determining whether the running average is within a predetermined threshold of a first ratio, wherein determining the length, type and starting position of the indel is performed responsive to a determination that the running average is within the predetermined threshold of the first ratio.

* * * * *